US008628476B2

(12) United States Patent
Utsuno et al.

(10) Patent No.: US 8,628,476 B2
(45) Date of Patent: Jan. 14, 2014

(54) BLOOD VESSEL STATE EVALUATING DEVICE, BLOOD VESSEL STATE EVALUATING METHOD, AND COMPUTER-READABLE RECORDING MEDIUM STORING BLOOD VESSEL STATE EVALUATING PROGRAM

(75) Inventors: Hideo Utsuno, Kyoto (JP); Shinya Umeda, Tokyo (JP); Hiroshi Matsuhisa, Kyoto (JP); Hironori Sato, Moriyama (JP); Toshihiko Ogura, Kyoto (JP)

(73) Assignee: OMRON HEALTHCARE Co., Ltd., Kyoto-shi, Kyoto (JP)

( * ) Notice: Subject to any disclaimer, the term of this patent is extended or adjusted under 35 U.S.C. 154(b) by 1075 days.

(21) Appl. No.: 12/531,407

(22) PCT Filed: Mar. 26, 2008

(86) PCT No.: PCT/JP2008/055677
§ 371 (c)(1),
(2), (4) Date: Oct. 7, 2009

(87) PCT Pub. No.: WO2008/120627
PCT Pub. Date: Oct. 9, 2008

(65) Prior Publication Data
US 2010/0121204 A1     May 13, 2010

(30) Foreign Application Priority Data

Mar. 30, 2007    (JP) ................................. 2007-092522

(51) Int. Cl.
*A61B 5/02*          (2006.01)
(52) U.S. Cl.
USPC ............ 600/483; 600/500; 600/504; 600/481
(58) Field of Classification Search
USPC ................................. 600/481, 483, 500, 485
See application file for complete search history.

(56) References Cited

U.S. PATENT DOCUMENTS

| 6,117,087 | A * | 9/2000 | Kamm et al. | 600/504 |
|---|---|---|---|---|
| 2003/0135124 | A1 * | 7/2003 | Russell | 600/500 |
| 2004/0097817 | A1 * | 5/2004 | Nakagawa | 600/500 |
| 2005/0234314 | A1 * | 10/2005 | Suzuki et al. | 600/301 |
| 2007/0276262 | A1 * | 11/2007 | Banet et al. | 600/485 |

(Continued)

FOREIGN PATENT DOCUMENTS

JP        2006-326334 A     12/2006

OTHER PUBLICATIONS

International Search Report w/translation from PCT/JP2008/055677 dated Apr. 22, 2008 (5 pages).

(Continued)

*Primary Examiner* — Michael Kahelin
*Assistant Examiner* — Tho Tran
(74) *Attorney, Agent, or Firm* — Osha Liang LLP

(57) ABSTRACT

A phase line tilt calculating unit (actual measurement) receives phase characteristics Pa(f) and Pb(f) outputted from frequency conversion units, and calculates phase difference characteristics of actual measurement based on a phase difference on each frequency component between the phase characteristics. A phase line tilt calculating unit (model) calculates phase difference characteristics between a transfer function Ga(f) and a transfer function Gb(f) calculated by a transfer function calculating unit, and outputs the calculated phase difference characteristics to a search unit. The search unit fits a variable k and determines a variable $k_{opt}$ (optimum solution) in which a tilt g(k) and a tilt $g_{exp}$ substantially match each other. The variable $k_{opt}$ is an index indicating a degree of arterial sclerosis of a subject.

14 Claims, 20 Drawing Sheets

(56) References Cited

U.S. PATENT DOCUMENTS

2008/0221461 A1* 9/2008 Zhou et al. .................... 600/485
2010/0317976 A1* 12/2010 Chelma et al. ................ 600/485

OTHER PUBLICATIONS

Utsuno, Hideo et al.; "Kekkan o Tsutawaru Myakuha no Denpan Sokudo Sokutei Hoho no Kenkyu" (translated as "Identification of Pulse Wave Velocity in Blood Vessel"); The Japan Society of Mechanical Engineers Dynamics and Design Conference 2006 CD-ROM Ronbunshu, The Japan Society of Mechanical Engineers, Aug. 6, 2006, No. 340 (6 pages).

Patent Abstracts of Japan; Publication No. 2006-326334 dated Dec. 7, 2006; Fukuda Denshi Co. Ltd. (1 page).

* cited by examiner (a)

(b)

(a) $S_T = 0$ (b) $S_T = 1$ (c) $S_T = -1$ (a)

(b)

(a) Coherence (b) Coherence (a)

(b)

(a)

(b)

(a)

Average pulse wave velocity (m/s)

Frequency (Hz)

(b)

Average pulse wave velocity (m/s)

Frequency (Hz)

BLOOD VESSEL STATE EVALUATING DEVICE, BLOOD VESSEL STATE EVALUATING METHOD, AND COMPUTER-READABLE RECORDING MEDIUM STORING BLOOD VESSEL STATE EVALUATING PROGRAM

TECHNICAL FIELD

The present invention relates to a blood vessel state evaluation device, a blood vessel state evaluation method, and a computer readable recording medium stored with a blood vessel state evaluation program for evaluating the state of a blood vessel constituting a living body, in particular, to a technique of modeling a blood vessel passage as a transfer function and evaluating a degree of arterial sclerosis of the blood vessel.

BACKGROUND ART

In recent years, circulatory system diseases caused by arterial sclerosis are increasing, and an evaluation device for evaluating a degree of arterial sclerosis of a blood vessel is accordingly being put to practical use. A pulse wave velocity method is known as a typical method of evaluating the degree of arterial sclerosis. The pulse wave velocity method uses a correlation between a velocity (pulse wave velocity) at which change in blood pressure involved in beating of a heart is propagated through the blood vessel and a degree of elastic force (rigidity) of the blood vessel. In other words, as a pulse wave advances through the blood vessel, which is an elastic tube, the pulse wave velocity increases the harder the tube wall, the narrower the inner diameter, and the thicker the tube thickness, and thus the degree of arterial sclerosis can be known by measuring the pulse wave velocity. In particular, an evaluation device by a baPWV method (brachial-ankle Pulse Wave Velocity method) using the time waveform of blood pressure at both upper arms and both angles is being put to practical use.

As a measurement method of the pulse wave velocity, Japanese Unexamined Patent Publication No. 2006-326334 (Patent Document 1) discloses a pulse wave propagation velocity measurement device including detection means for detecting a temporal distortion between voltage waveforms obtained from adjacent voltage electrode pairs out of a plurality of voltage waveforms, and calculating means for obtaining a rate of change of the pulse wave propagation velocity or the pulse wave propagation time between the adjacent voltage electrodes using a distance between the adjacent voltage electrodes and/or a temporal shift for all of the plurality of voltage waveforms.

Patent Document 1: Japanese Unexamined Patent Publication No. 2006-326334

DISCLOSURE OF THE INVENTION

Problems to be Solved by the Invention

As described in Japanese Unexamined Patent Publication No. 2006-326334 (Patent Document 1), a time difference (delay time) between time waveforms measured at a plurality of points on a blood vessel passage is obtained, and a pulse wave velocity is calculated by dividing a passage difference from a heart of each point with the relevant time difference, for the method of measuring the pulse wave velocity.

However, since the actual pulse wave velocity depends on a propagation passage and frequency, an accurate pulse wave velocity cannot be calculated by simply dividing the passage difference with the time difference. In other words, a value shifted from the original pulse wave velocity is sometimes calculated depending on a blood vessel diameter and a blood vessel length of a subject, a frequency component contained in the pulse wave, and the like. Thus, evaluation accuracy of a degree of arterial sclerosis cannot be raised.

In view of solving the above problems, the present invention aims to provide a blood vessel state evaluation device, a blood vessel state evaluation method, and a computer readable recording medium stored with a blood vessel state evaluation program capable of evaluating the degree of arterial sclerosis at higher accuracy.

Means for Solving the Problems

In accordance with one aspect of the present invention, a blood vessel state evaluation device includes a storage unit, a first measurement unit, a second measurement unit, a first calculating unit, a second calculating unit, and a search unit. The storage unit stores a circulatory system model in which a blood vessel constituting a living body is divided into a plurality of zones and modeled, the circulatory system model including a shape value representing each of the plurality of zones. The first measurement unit, attached to a first measurement site of the living body, measures a time waveform of a first biological signal. The second measurement unit, attached to a second measurement site of the living body, measures a time waveform of a second biological signal in synchronization with the first measurement unit. The first calculating unit calculates a phase difference characteristics of actual measurement based on a phase difference on each frequency component between the first biological signal and the second biological signal. The second calculating unit calculates a phase difference characteristics between a first transfer function defined based on the circulatory system model in correspondence to a blood vessel passage to the first measurement site and a second transfer function defined based on the circulatory system model in correspondence to a blood vessel passage to the second measurement site. The first transfer function and the second transfer function include an elasticity variable indicating a degree of elastic force of the blood vessel. The search unit determines the elasticity variable by fitting the phase difference characteristics calculated by the second calculating unit based on the phase difference characteristics of actual measurement calculated by the first calculating unit.

Preferably, the blood vessel state evaluation device further includes a transfer function calculating unit for calculating the first and second transfer functions based on the shape value of each zone corresponding to the blood vessel passages to the first and second measurement sites, respectively.

More preferably, the transfer function calculating unit calculates the first and second transfer functions using a distribution constant model, having a blood pressure of the blood vessel and a blood flow rate as input variables, corresponding to each zone; and each distribution constant model includes a vertical impedance corresponding to easiness in flowing of blood in the corresponding zone, and a horizontal impedance including the elasticity variable.

Preferably, the blood vessel state evaluation device further includes a pulse wave velocity calculating unit for calculating a pulse wave velocity in the blood vessel based on the elasticity variable fitted by the search unit.

More preferably, the pulse wave velocity calculating unit calculates the pulse wave velocity based on the shape value of each zone corresponding to the blood vessel passage to the first measurement site and the shape value of each zone corresponding to the blood vessel passage to the second measurement site.

Preferably, the circulatory system model includes a blood vessel diameter and a blood vessel length for the shape value.

Preferably, the circulatory system model is obtained by classifying the blood vessel constituting the living body to a plurality of sections, and then modeling the blood vessel belonging to at least one section of the plurality of sections.

More preferably, the blood vessel constituting the living body is classified to the plurality of sections based on a size of a blood vessel diameter.

Preferably, the transfer function calculating unit adds a peripheral part model, in which a blood vessel not modeled in the circulatory system model of the blood vessels contained in each zone is modeled, to the circulatory system model corresponding to each zone, and then calculates the transfer function.

More preferably, the transfer function calculating unit converts the circulatory system model of each zone based on a shape difference of the blood vessel to calculate the peripheral part model of the zone.

Still more preferably, the transfer function calculating unit calculates the transfer function with a terminating end of the peripheral part model under a non-reflection condition.

Preferably, the blood vessel state evaluation device further includes a first frequency conversion unit for calculating first phase characteristics indicating the phase on each frequency component from the first biological signal; and a second frequency conversion unit for calculating second phase characteristics indicating the phase on each frequency component from the second biological signal. The first calculating unit calculates differential phase data by taking a difference of the first phase data and the second phase data. In addition, the first calculating unit calculates the phase difference characteristics of actual measurement by correcting a phase shift caused by a period delay in the differential phase data in units of phase corresponding to one or more periods.

Preferably, the first calculating unit calculates the phase difference characteristics of actual measurement using a frequency component in which a coherence value between the first biological signal and the second biological signal is higher than a threshold value defined in advance.

In accordance with another aspect of the present invention, there is provided a blood vessel state evaluation method for evaluating a state of a blood vessel constituting a living body using a circulatory system model in which the blood vessel constituting the living body is divided into a plurality of zones and modeled. The circulatory system model includes a shape value representing each of the plurality of zones. The blood vessel state evaluation method includes the steps of: measuring a time waveform of a first biological signal from a first measurement site of the living body and measuring a time waveform of a second biological signal from a second measurement site of the living body; calculating a phase difference characteristics of actual measurement based on a phase difference on each frequency component between the first biological signal and the second biological signal; calculating a phase difference characteristics between a first transfer function defined based on the circulatory system model in correspondence to a blood vessel passage to the first measurement site and a second transfer function defined based on the circulatory system model in correspondence to a blood vessel passage to the second measurement site. The first transfer function and the second transfer function include an elasticity variable indicating a degree of elastic force of the blood vessel. The blood vessel state evaluation method further includes the step of determining the elasticity variable by fitting the phase difference characteristics between the first transfer function and the second transfer function based on the phase difference characteristics of actual measurement.

In accordance with still another aspect of the present invention, there is provided a computer readable recording medium stored with a blood vessel state evaluation program for evaluating a state of a blood vessel constituting a living body using a circulatory system model in which the blood vessel constituting the living body is divided into a plurality of zones and modeled. The circulatory system model includes a shape value representing each of the plurality of zones. A calculation processing unit performs, in response to a command from the program, the steps of acquiring a time waveform of a first biological signal at a first measurement site of the living body and acquiring a time waveform of a second biological signal at a second measurement site of the living body; calculating a phase difference characteristics of actual measurement based on a phase difference on each frequency component between the first biological signal and the second biological signal; and calculating a phase difference characteristics between a first transfer function defined based on the circulatory system model in correspondence to a blood vessel passage to the first measurement site and a second transfer function defined based on the circulatory system model in correspondence to a blood vessel passage to the second measurement site. The first transfer function and the second transfer function include an elasticity variable indicating a degree of elastic force of the blood vessel. The calculating processing unit determines the elasticity variable by fitting the phase difference characteristics between the first transfer function and the second transfer function based on the phase difference characteristics of actual measurement.

Effects of the Invention

According to the present invention, a blood vessel state evaluation device, a blood vessel state evaluation method, and a computer readable recording medium stored with a blood vessel state evaluation program capable of evaluating a degree of arterial sclerosis at higher accuracy are realized.

BRIEF DESCRIPTION OF THE DRAWINGS

FIG. 5($b$) is a view in which the physical model shown in FIG. 5($a$) is replaced with an electrical equivalent circuit.

Figure 1:
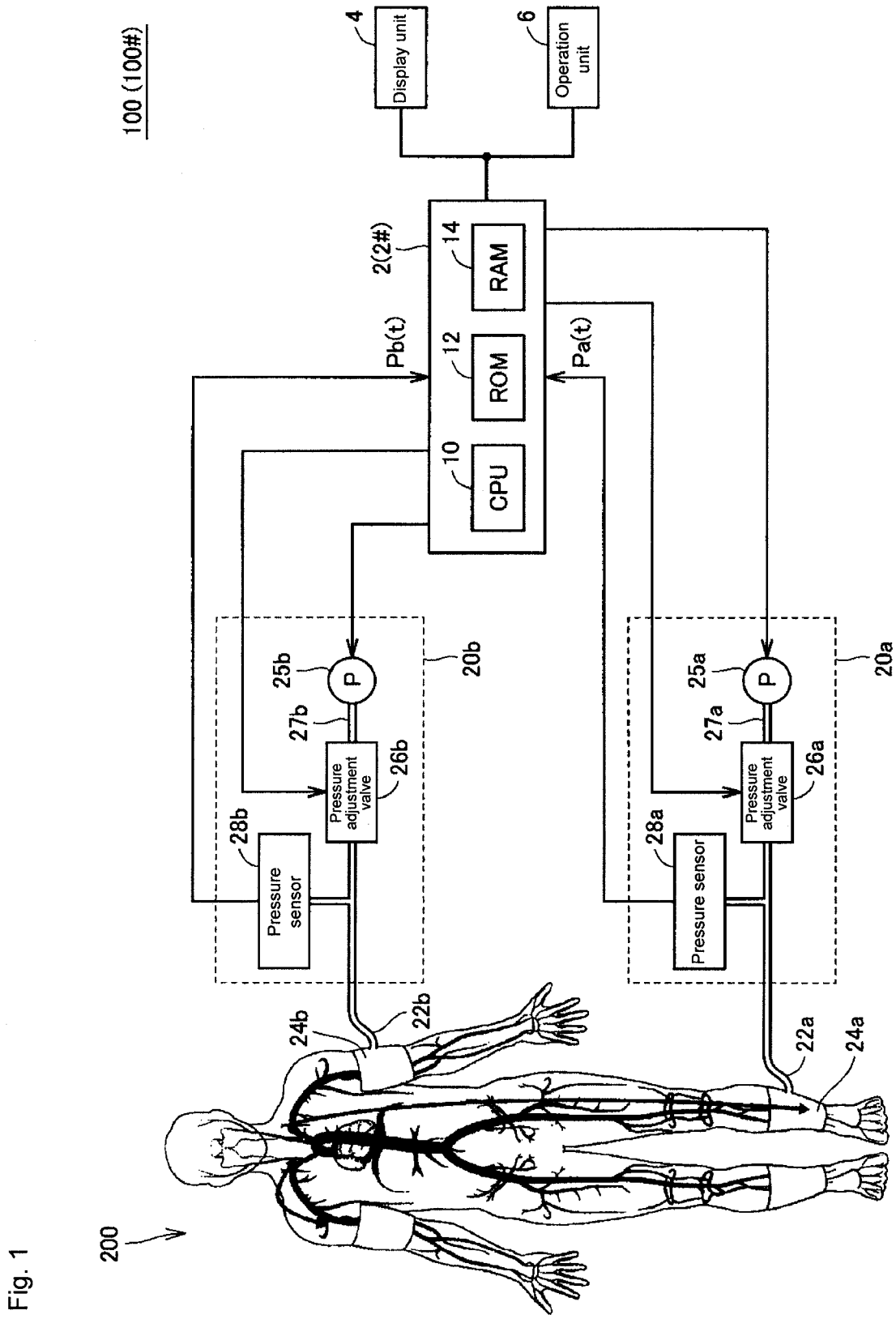
FIG. 1 is a schematic configuration view of a blood vessel state evaluation device according to a first embodiment of the present invention.

DESCRIPTION OF THE REFERENCE SYMBOLS 2, 2# Control unit
4 Display unit
6 Operation unit
10 CPU
12 ROM
14 RAM
20a, 20b Measurement unit
22a, 22b, 27a, 27b Piping
24a, 24b Pressing cuff
25a, 25b Pressure pump
26a, 26b Pressure adjustment valve
28a, 28b Pressure sensor
30a, 30b Frequency conversion unit (FFT)
32 Phase line tilt calculating unit (actual measurement)
34 Circulatory system model
36 Transfer function calculating unit
38 Phase line tilt calculating unit (model)
40 Search unit
42, 48 Evaluation unit
44 Pulse wave velocity model calculating unit
46 Average pulse wave velocity calculating unit
50 Test volume
100, 100# Blood vessel state evaluation device (evaluation device)

BEST MODE FOR CARRYING OUT THE INVENTION

Embodiments of the present invention will be described in detail with reference to the drawings. Same reference numerals are denoted for the same or corresponding portions in the figure, and the description thereof will not be repeated.

First Embodiment

Device Configuration

With reference to FIG. 1, a blood vessel state evaluation device (hereinafter also referred to simply as "evaluation device") 100 according to a first embodiment of the present invention includes a control unit 2, a display unit 4, an operation unit 6, and measurement units 20a, 20b.

The control unit 2 is a device for controlling the entire evaluation device 100, and is typically configured by a computer including a CPU (Central Processing Unit) 10, a ROM (Read Only Memory) 12, and a RAM (Random Access Memory) 14.

The CPU 10 corresponds to a calculation processing unit, and reads out a program stored in advance in the ROM 12, and executes a command described in the program while using the RAM 14 as a work memory. The ROM 12 is stored in advance with at least a circulatory system model, to be hereinafter described, and the CPU 10 references the circulatory system model when executing the program stored with the blood vessel state evaluation method according to the present embodiment.

The display unit 4 and the operation unit 6 are connected to the control unit 2. The display unit 4 urges input of various types of setting by the user or displays the calculation result from the control unit 2. The user operates the operation unit 6 while checking the content displayed on the display unit 4 and inputs the desired setting. The display unit 4 may be LED (Light Emitting Diode) or LCD (Liquid Crystal Display), by way of example.

More specifically, the control unit 2 gives a measurement command to the measurement units 20a, 20b, receives measurement signals Pa(t), Pb(t) measured in response to the measurement command, and executes the blood vessel state evaluation method according to the present embodiment based on the measurement signals Pa(t), Pb(t).

The measurement units 20a, 20b increase an inner pressure (hereinafter referred to as "cuff pressure") of pressing cuffs (air bags) 24a, 24b attached to predetermined measurement sites of a subject 200, and measure a time waveform of a biological signal (e.g., pulse wave) at the respective measurement site. As described below, the control unit 2 calculates phase difference characteristics of an actual measurement based on a phase difference on each frequency component between the measurement signal Pa(t) and the measurement signal Pb(t), and thus the measurement command is simultaneously given from the control unit 2 such that the measurement units 20a and 20b can measure the biological signal in synchronization to each other.

More specifically, for example, the pressing cuffs 24a and 24b are attached to an ankle and an upper arm, respectively, of the subject 200 and are pressurized by air supplied from the measurement units 20a and 20b through piping 22a and 22b. Such pressurization presses the pressing cuffs 24a and 24b against the corresponding measurement sites, and the pressure change corresponding to the pulse wave of the measurement site is transmitted to the measurement units 20a and 20b through the piping 22a and 22b. The measurement units 20a, 20b measure the time waveform of the pulse wave of the measurement site by detecting the transmitted pressure change. The calculation process is preferably performed on the predetermined frequency component (e.g., 0 to 20 [Hz]) of the measurement signals Pa(t) and Pb(t), and thus the measurement period (sampling period) of the measurement signals Pa(t) and Pb(t) is preferably shorter than a time interval (e.g., 25 msec) corresponding to such frequency component.

In order to execute the measurement operation, the measurement unit 20a includes a pressure sensor 28a, a pressure adjustment valve 26a, a pressure pump 25a, and a piping 27a. The pressure sensor 28a is a detection site for detecting the pressure fluctuation transmitted through the piping 22a, and includes a plurality of sensor elements arrayed at a predetermined interval on a semiconductor chip including monocrystal silicon and the like, by way of example. The pressure adjustment valve 26a is interposed between the pressure pump 25a and the pressing cuff 24a, and maintains the pressure used in pressurization of the pressing cuff 24a during measurement to a predetermined range. The pressure pump 25a operates in response to the measurement command from the control unit 2, and supplies pressurizing air for pressurizing the pressing cuff 24a.

Similarly, the measurement unit 20b includes a pressure sensor 28b, a pressure adjustment valve 26b, a pressure pump 25b, and a piping 27b. The configuration of each part is similar to that of the measurement unit 20a, and thus detailed description thereof will not be repeated.

In the present embodiment, a configuration of measuring, as a biological signal, the pressure change caused by the pulse wave using the pressure cuff will be described, but a very small constant current may be flowed to the measurement site of the subject 200, and the voltage change caused by the change in impedance (biological impedance) that occurs according to the propagation of the pulse wave may be measured as the biological signal.

In a correspondence relationship of the evaluation device 100 shown in FIG. 1 and the subject invention, the measurement unit 20a, the piping 22a, and the pressing cuff 24a correspond to "first measurement unit", and the measurement unit 20b, the piping 22b, and the pressing cuff 24b correspond to "second measurement unit".

(Function Block Diagram)

The control unit 2 calculates two transfer functions defined in correspondence to the blood vessel passages to the measurement site where the pressing cuffs 24a and 24b are attached based on the circulatory system model stored in advance. In this case, each transfer function includes an elasticity variable indicating an elastic force degree of the blood vessel. In other words, the elasticity variable is an index indicating a degree of arterial sclerosis of the blood vessel. In the present embodiment, the "Young's modulus" is used as a typical example of the elasticity variable, but other variables indicating rigidity and flexibility of the blood vessel may be used. The control unit 2 converts the measurement signals Pa(t) and Pb(t) to the signal of the frequency region, and then calculates the phase difference characteristics of the actual measurement between them, and fits (identifies) the elasticity variable such that the phase difference characteristics of the actual measurement match the phase difference characteristics between two transfer functions. The fit elasticity variable becomes the value indicating the degree of arterial sclerosis of the subject 200. Function blocks for realizing such a processing operation in the control unit 2 will be described below.

Figure 2:
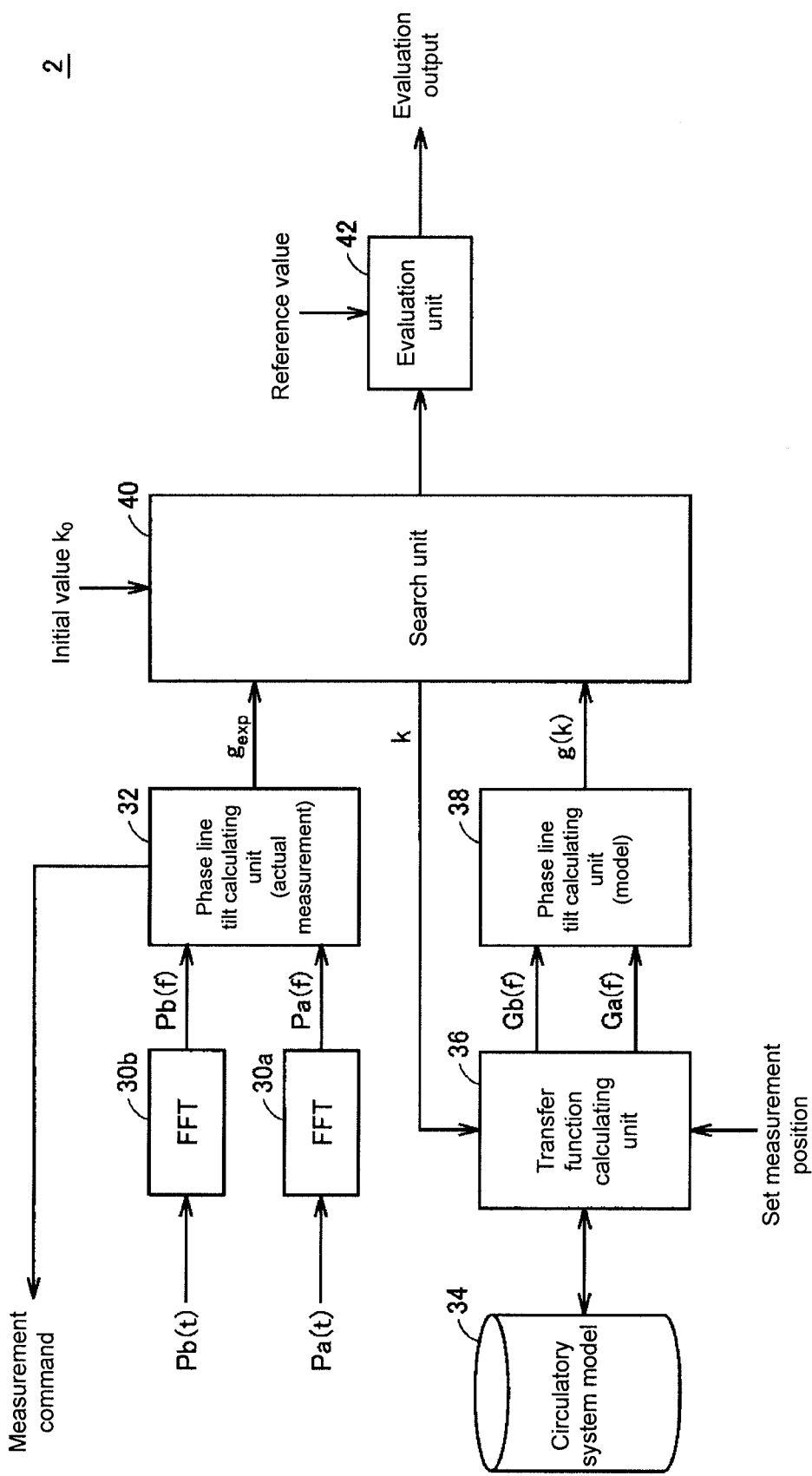
FIG. 2 is a function block diagram schematically showing functions executed by a control unit of the blood vessel state evaluation device according to the first embodiment of the present invention.

FIG. 2 is a function block diagram schematically showing the functions executed by the control unit 2 of the blood vessel state evaluation device 100 according to the first embodiment of the present invention.

With reference to FIG. 2, the control unit 2 includes frequency conversion units (FFT) 30a, 30b, phase line tilt calculating unit (actual measurement) 32, a storage unit 34, a transfer function calculating unit 36, a phase line tilt calculating unit (model) 38, a search unit 40, and an evaluation unit 42 as control structures.

The frequency conversion units 30a and 30b respectively accumulate the measurement signals Pa(t) and Pb(t) or time waveforms over a predetermined period, and convert the accumulated measurement signals Pa(t) and Pb(t) to the function of the frequency region. Typically, the frequency conversion units 30a and 30b execute frequency conversion using the Fast Fourier Transformer (FFT). Note that the present invention is not limited to the fast Fourier transformer, but any logic may be used as long as the function of time region is transformed to a function of frequency region such as Fourier series.

The frequency conversion unit 30a calculates the phase characteristics Pa(f) indicating the phase on each frequency component of the measurement signal Pa(t), and outputs the calculated phase characteristics Pa(f) to the phase line tilt calculating unit (actual measurement) 32. Similarly, the frequency conversion unit 30b calculates the phase characteristics Pb(f) indicating the phase on each frequency component of the measurement signal Pb(t), and outputs the calculated phase characteristics Pb(f) to the phase line tilt calculating unit (actual measurement) 32.

The phase line tilt calculating unit (actual measurement) 32 gives a measurement command to the measurement units 20a, 20b in response to an operation of the operation unit 6 (FIG. 1) by a user. After giving the measurement command, the phase characteristics Pa(f) and the phase characteristics Pb(f) outputted from the frequency conversion units 30a and 30b are received, and the phase difference characteristics of the actual measurement is calculated based on the phase difference on each frequency component between the phase characteristics. Specifically, the phase line tilt calculating unit (actual measurement) 32 compares the values of the phase characteristics Pa(f) and Pb(f) for every frequency component, and calculates the phase difference between the phase characteristics. As described below, the phase difference calculated in such a manner can be approximated as a primary function for the frequency, and thus the tilt $g_{exp}$ [deg/Hz] of the approximated primary function (phase line) can be outputted to the search unit 40 as the phase difference characteristics of the actual measurement. In other words, the tilt $g_{exp}=\tan(\phi_{exp})$ is defined using the deflection angle φ calculated as the deflection angle $\phi_{exp}=\angle$(phase characteristics Pa(f)/phase characteristics Pb(f)).

The transfer function calculating unit 36 calculates two transfer functions Ga(f) and Gb(f) indicating the transfer characteristics of the blood vessel passages from a heart to two measurement sites where the pressing cuffs 24a and 24b are attached, and outputs the result to the phase line tilt calculating unit (model) 38. More specifically, the transfer function calculating unit 36 calculates the pulse wave propagation model (transfer function) with respect to the entire body having the heart as an input end based on the circulatory system model stored in advance in the storage unit 34, and calculates the transfer functions Ga(f) and Gb(f) corresponding to the blood vessel passages to the two measurement sites in the pulse wave propagation model of the entire body. In this case, a Young's modulus is incorporated in the transfer functions Ga(f) and Gb(f) in a form of including a variable k, where a specific value is set to the variable k by the search unit 40.

The storage unit 34 stores the circulatory system model in which the blood vessel of the subject 200 is divided into a plurality of zones and modeled. The circulatory system model is defined with a shape value representing each zone in correspondence to each zone. Examples of such a shape value include a blood vessel diameter, a blood vessel length, and a thickness of the blood vessel wall of each zone in the present embodiment. The circulatory system model will be described below in detail.

The phase line tilt calculating unit (model) 38 calculates the phase difference characteristics of the transfer function Ga(f) and the transfer function Gb(f), and outputs the calculated phase difference characteristics to the search unit 40. Specifically, the phase line tilt calculating unit (model) 38 outputs the tilt g(k) [deg/Hz] of the phase line or the phase difference between the phase characteristics Ga(f) and the phase characteristics Gb(f) in the frequency region to the search unit 40 as phase difference characteristics. The tilt g(k) is defined as the tilt $g(k)=\tan(\phi_{model})$ using the deflection angle $\phi_{model}$ calculated as the deflection angle $\phi_{model}=\angle$(transfer function Ga(f)/transfer function Gb(f)).

The search unit 40 fits the tilt g(k) calculated by the phase line tilt calculating unit (model) 38 based on the tilt $g_{exp}$ calculated by the phase line tilt calculating unit (actual measurement) 32 to determine the variable k. In other words, the variable k is sequentially changed from an initial value $k_0$ until the tilt g(k) and the tilt $g_{exp}$ substantially match each other, and the calculation process in the transfer function calculating unit 36 and the phase line tilt calculating unit (model) 38 is repeatedly executed. When the variable $k_{opt}$ (optimum solution) in which the tilt g(k) and the tilt $g_{exp}$ substantially match is determined, the search unit 40 outputs the value of the determined variable k to the evaluation unit 42. The determined optimum solution of the variable k becomes an index indicating the degree of arterial sclerosis of the subject 200.

The evaluation unit 42 compares the optimum solution $k_{opt}$ (or the Young's modulus converted using the optimum solution $k_{opt}$) determined in the search unit 40 with a reference value defined in advance, and outputs the evaluation on the degree of arterial sclerosis to the display unit 4 (FIG. 1), and the like.

The operations and configurations of the main functions will be described in detail below.

(Physical Model)

As described above, the transfer function calculating unit 36 calculates the transfer function indicating the transfer characteristics of the blood vessel passage having the heart as the input end (starting point), where the calculated transfer function is analytically calculated from a dynamic model in which the pulse wave propagates through the blood vessel. In the present embodiment, a configuration in which each zone of the blood vessel is one-dimensional linear distribution constant modeled to calculate the transfer function will be described.

First, with the blood vessel as an axial symmetric thin-thickness circular tube that microscopically deforms, a flow of internal blood as a layer flow of nonviscous fluid, and modeling performed assuming that the reflected wave does not exist, a relationship between a pulse wave velocity $C_p$ and a Young's modulus E of the blood vessel wall is represented with equation (1) called a Moens-Korteweg equation. The pulse wave velocity $C_p$ is a velocity at which a change in blood pressure involved in beating of the heart propagates the blood vessel.

[Formula 1]

$$C_p = \sqrt{\frac{Eh}{2r\rho}} \quad (1)$$

Where h is a thickness of the tube wall, r is an inner diameter of the vessel, and ρ is a density of the blood.

From equation (1), it can be seen that the pulse wave velocity $C_p$ increases the harder the blood vessel, the narrower the lumen, and thicker the blood vessel wall.

Figure 3:
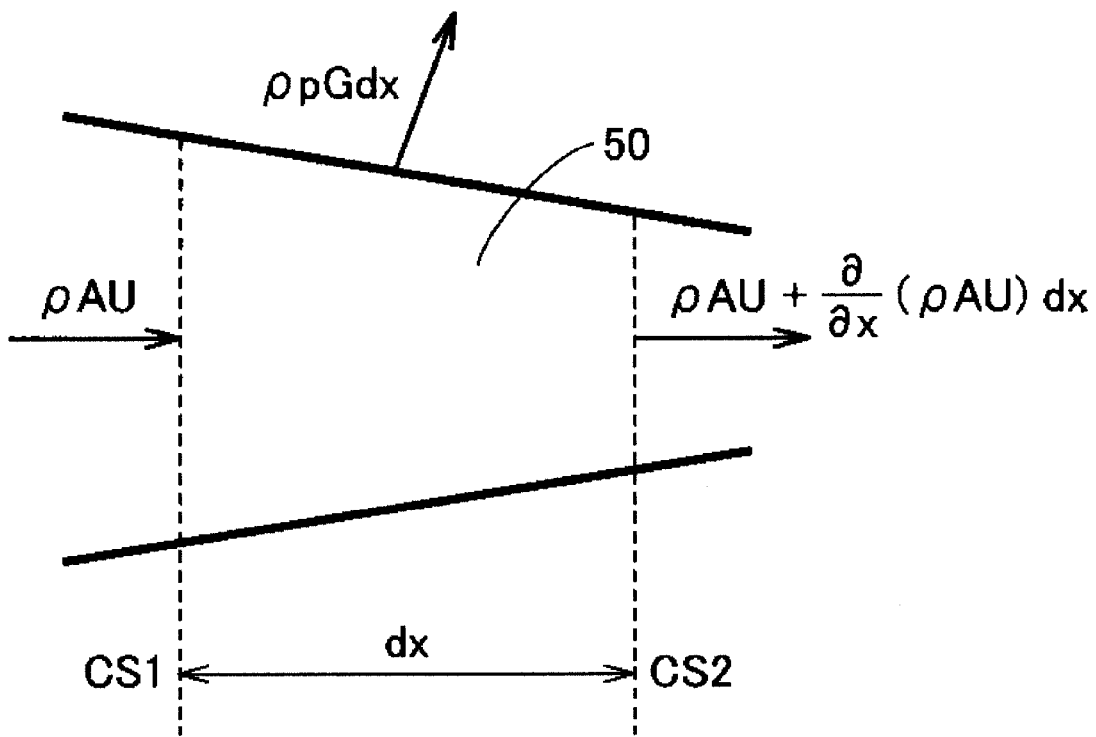
FIG. 3 is a view showing a one-dimensional flow model of blood in a blood vessel.

FIG. 3 is a view showing a one-dimensional flow model of the blood in the blood vessel.

Generally, since the volume elasticity of the blood is sufficiently high compared to the blood vessel, the blood vessel can be considered as an elastic circular tube and the blood as an incompressible fluid. The dominant equation of the one-dimensional flow in the elastic tube is derived as below.

With reference to FIG. 3, consider conserving a mass related to a test volume 50 between cross-sections CS1-CS2 of the one-dimensional flow model. With area of the lumen of the cross-section CS1 as A ($=\pi r_i^2$), the density of the fluid (blood) as ρ, the pressure as p, the cross-sectional average flow velocity as U, and the volume of the fluid flowing out in units of time to the branched blood vessel between the cross-sections CS1-CS2 is G per unit length and unit pressure, equation (2) is satisfied due to law of conservation of mass. Since the density ρ is constant in the incompressible fluid, equation (2) can be simplified to equation (3).

[Formula 2]

$$\frac{\partial(\rho A)}{\partial t} + \frac{\partial(\rho A U)}{\partial x} + \rho p G = 0 \quad (2)$$

$$\frac{\partial A}{\partial t} + \frac{\partial(AU)}{\partial x} + pG = 0 \quad (3)$$

Figure 4:
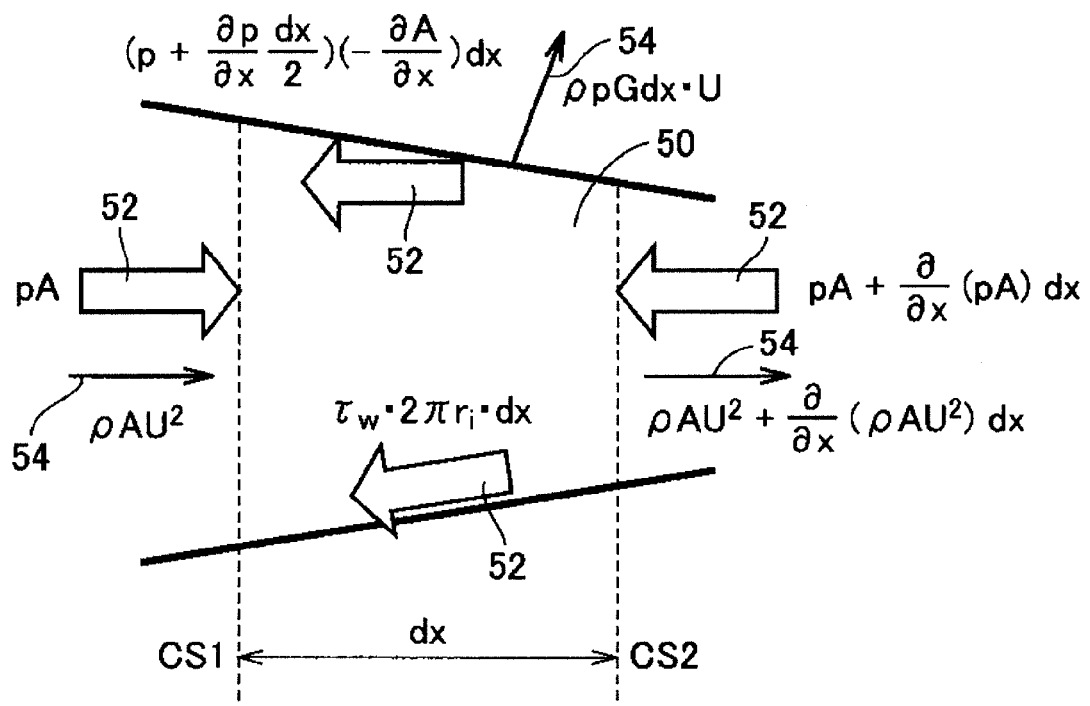
FIG. 4 is a view showing a force that acts on a test volume shown in FIG. 3 and a kinetic momentum that flows in and out.

FIG. 4 is a view showing a force 52 that acts on the test volume 50 shown in FIG. 3 and a kinetic momentum 54 that flows in and out.

With reference to FIG. 4, the change per unit time of the kinetic momentum 54 in the test volume 50 is equal to the net kinetic momentum 54 that flows in and the force 52 that influences the test volume 50. Thus, the minor terms of high order can be omitted to derive equation (4).

[Formula 3]

$$\rho\frac{\partial(AU)}{\partial t} + \rho\frac{\partial(AU^2)}{\partial x} + \rho p GU + A\frac{\partial p}{\partial x} + 2\pi r_i \tau_w = 0 \quad (4)$$

Where $t_w$ is a shear frictional stress at the wall surface and $r_1$ is a radius of the lumen.

The motion equation shown in equation (5) is obtained by organizing equation (4) using equation of continuity.

[Formula 4]

$$\rho\frac{\partial U}{\partial t} + \rho U\frac{\partial U}{\partial x} + \frac{\partial p}{\partial x} + \frac{2\pi r_i \tau_w}{A} = 0 \quad (5)$$

In order to perform one-dimensional linear distribution constant modeling on the blood vessel, the nonlinear terms in equation (3) and equation (5) are omitted, and the variable is replaced with the pressure p and a volumetric flow rate q (=AU) to obtain equations (6) and (7).

[Formula 5]

$$-\frac{\partial p}{\partial x} = Rq + L\frac{\partial q}{\partial t} \quad (6)$$

$$-\frac{\partial q}{\partial x} = Gp + C\frac{\partial p}{\partial t} \quad (7)$$

Here, regarding physical meaning of the four coefficients in equation (6) and equation (7), R indicates a viscosity resistance of when the blood flows, L indicates an inertia of blood to inhibit sudden change when the flow changes, G indicates easiness in flowing of the blood that flows out to the outside of the blood vessel or to the branched tube, and C indicates an ability of accumulating blood in the blood vessel when the blood vessel expands or contracts according to the pressure change.

Figure 5:
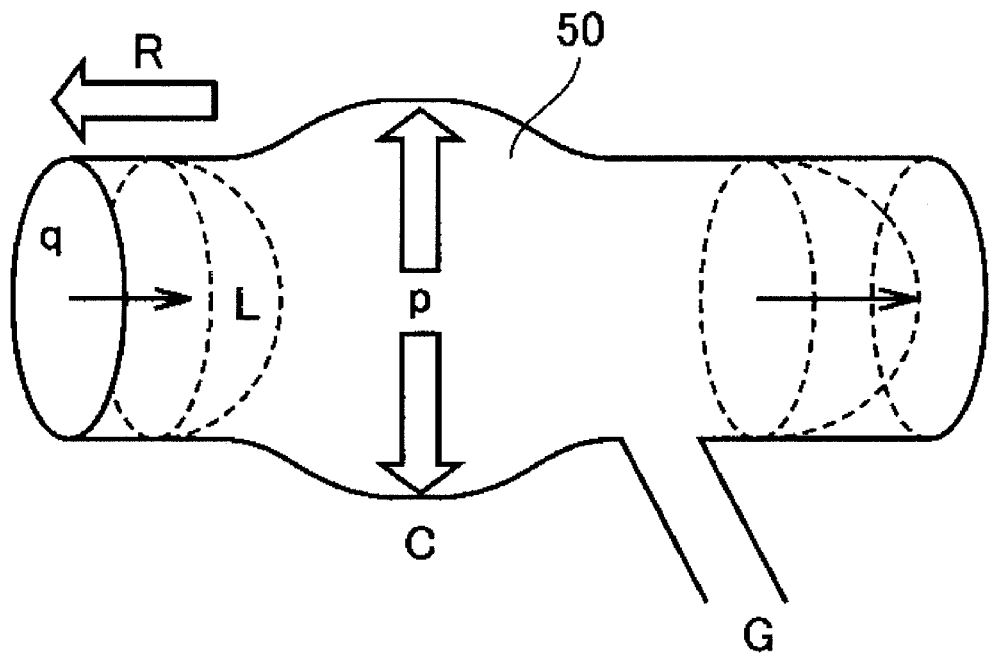
FIG. 5($a$) is a schematic view in which the blood vessel is performed with one-dimensional linear distribution constant modeling.
Figure 5:
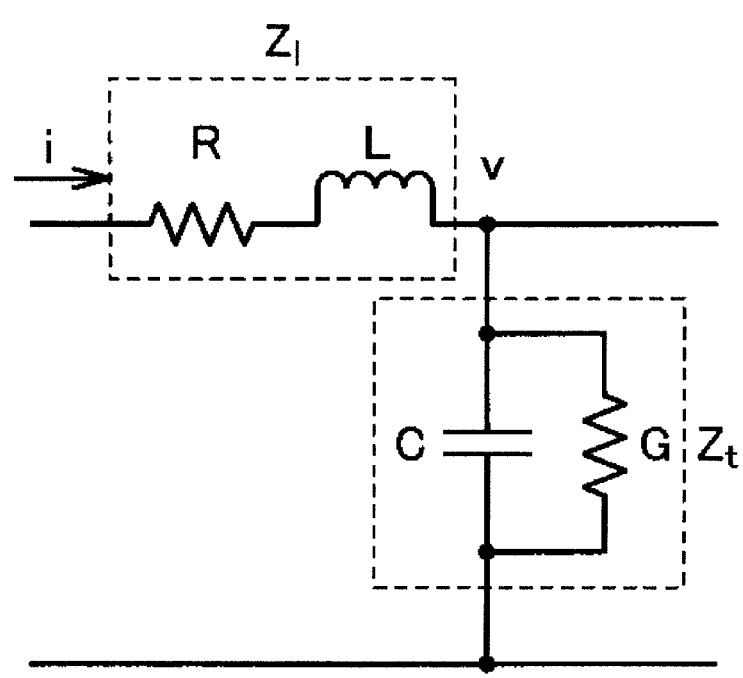

FIG. 5 is a schematic view in which the blood vessel is subjected to one-dimensional linear distribution constant modeling. FIG. 5(a) is a view in which equation (6) and equation (7), and the physical model of the blood vessel are corresponded. FIG. 5(b) is a view in which the physical model shown in FIG. 5(a) is replaced with an electrical equivalent circuit.

In other words, equation (6) and equation (7) can be corresponded with the physical model as shown in FIG. 5(a). Furthermore, in equation (6) and equation (7), the pressure p is replaced with a voltage v and the flow rate g is replaced with current i to realize the electrical equivalent circuit (distribution constant circuit) as shown in FIG. 5(b). Here, R indicates a resistance, L indicates an inductance, G indicates an admittance, and C indicates a capacitance.

Equation (6) corresponds to the motion equation in the blood vessel system and corresponds to Ohm's Law in an electrical system. A phenomenon in which the fluid is accelerated by a pressure gradient between the cross-section CS1 and the cross-section CS2 in the blood vessel system corresponds to a phenomenon in which the potential difference applied to both ends of the inductance causes current in the electrical system.

Equation (7) corresponds to equation of continuity (law of conservation of mass) in the blood vessel system, and corresponds to law of conservation of charge in the electrical system. In the blood vessel system, a phenomenon in which the accumulated amount of mass that cannot advance from the cross-section CS1 to the cross-section CS2 pushes and opens the blood vessel thereby causing a rise of pressure corresponds to a phenomenon in which the charges accumulated in the capacitor causes a rise of voltage.

Furthermore, in equation (6) and equation (7), the relational expression shown in equation (8) and equation (9) is derived when $p=Pe^{jwt}$ and $q=Qe^{jwt}$.

[Formula 6]

$$-\frac{\partial P}{\partial x} = (R + j\omega L)Q = Z_l Q \quad (8)$$

$$-\frac{\partial Q}{\partial x} = (G + j\omega C)P = \frac{1}{Z_t}P \quad (9)$$

Where ω is an angular frequency.

In the present specification, $Z_l$ (=r+jωL) shown in FIG. 5(b) and equation (8) is referred to as "vertical impedance", and $Z_t$ (=(G+jωC)$^{-1}$) shown in FIG. 5(b) and equation (9) is referred to as "horizontal impedance". A general solution of equation (8) and equation (9) becomes equation (10) and equation (11), respectively, with an amplitude value of a traveling wave of the pressure at x=0 as $P_f$ and an amplitude value of a receding wave as $P_r$. A relationship of ω=2πf is satisfied between the angular frequency ω and the frequency f.

[Formula 7]

$$P = P_f e^{-\gamma x} + P_r e^{\gamma x} \qquad (10)$$

$$Q = \frac{1}{Z_0}(P_f e^{-\gamma x} - P_r e^{\gamma x}) \qquad (11)$$

Where $\gamma$ is a propagation constant, and $Z_0$ is a characteristic impedance.

The propagation constant $\gamma$ is expressed as in equation (12) using an attenuation constant $\beta$ and the phase velocity (pulse wave velocity) $C_p$.

[Formula 8]

$$\gamma = \sqrt{\frac{Z_l}{Z_t}} = \beta + j\frac{\omega}{C_p} \qquad (12)$$

Here, the phase velocity $C_p$ is the amount indicating the distance the pulse wave advances in unit time, and the attenuation constant $\beta$ indicates that the amplitude of the pulse wave becomes $e^{-\beta}$ times for every advancement of unit distance. The characteristic impedance $Z_0$ can be expressed as equation (13), and indicates the pressure necessary for advancing the pulse wave of unit volume in an advancing direction.

[Formula 9]

$$Z_0 = \sqrt{Z_l Z_t} \qquad (13)$$

Furthermore, pressures $P_s$, $P_e$ and volumetric flow rates $Q_s$, $Q_e$ at two points spaced apart by distance $l_{se}$ are associated with a transfer matrix of equation (14).

[Formula 10]

$$\begin{Bmatrix} P_s \\ Q_s \end{Bmatrix} = \begin{bmatrix} \cosh\gamma l_{se} & Z_0 \sinh\gamma l_{se} \\ \frac{1}{Z_0}\sinh\gamma l_{se} & \cosh\gamma l_{se} \end{bmatrix} \begin{Bmatrix} P_e \\ Q_e \end{Bmatrix} \qquad (14)$$

In the present embodiment, the transfer matrix shown in equation (14) is calculated in correspondence to each zone of the blood vessel, and the transfer function is calculated by connecting in cascade the transfer matrix corresponding to each zone according to the target blood vessel passage. In this case, the condition of the downstream from the arbitrary boundary is expressed with an impedance $Z_x$ of equation (15), which is a ratio of a pressure $P_x$ and a volume velocity $Q_x$ at the relevant boundary.

[Formula 11]

$$Z_x = \frac{P_x}{Q_x} \qquad (15)$$

A reflectivity $S_p$, which is a ratio of the amplitude of the traveling wave and the receding wave, is expressed with equation (16).

[Formula 12]

$$S_p = \frac{P_r}{P_f} = \frac{Z_x - Z_0}{Z_x + Z_0} = \frac{1 - \frac{Z_0}{Z_x}}{1 + \frac{Z_0}{Z_x}} \qquad (16)$$

(Calculation of Vertical Impedance)

The vertical impedance $Z_l$ includes the terms of the viscosity resistance and the inertia of the fluid, and is obtained by modeling the flow velocity distribution in the blood vessel cross-section.

In the present embodiment, the vertical impedance is calculated based on the Womersley model. The Womersley model represents the flow velocity distribution in a state the pulse wave flow in the circular tube of a Newtonian fluid is sufficiently developed. The vertical impedance based on the Womersley model is expressed with equation (17) using a first kind Bessel function $J_n$.

[Formula 13]

$$Z_l = \frac{j\omega \frac{\rho}{\pi r_i^2}}{1 - \frac{2J_1(\alpha\sqrt{-j})}{\alpha\sqrt{-j}\, J_0(\alpha\sqrt{-j})}} \qquad (17)$$

Where $\rho$ is the density of the blood, $r_i$ is the inner diameter of the tube, and $\mu$ is a viscosity coefficient of the blood.

$$\alpha = \sqrt{r_i^2 \rho \omega / \mu}$$

Here, $\alpha$ in equation (17) is referred to as "Womersley alpha" and is the amount indicating the ratio of the viscosity term and the inertia term of the pulse wave flow, and corresponds to the Reynolds number in a steady flow. The density $\rho$ of the blood is typically $1.03 \times 10^3$ [g/m$^3$], and the viscosity coefficient $\mu$ of the blood is typically $4 \times 10^{-3}$ [Pa·s].

A non-viscous model may be used in place of the Womersley model shown in equation (17). In this model, the blood is a non-viscous fluid and the flow velocity in cross-section is constant. The vertical impedance based on the non-viscous model is expressed with equation (18).

[Formula 14]

$$Z_l = j\omega \frac{\rho}{A} \qquad (18)$$

Furthermore, a Poiseuille model may be used in place of the above model. This model represents the flow velocity distribution in a state the steady flow in the circular tube of the Newtonian fluid is sufficiently developed. The vertical impedance based on the Poiseuille model is expressed with equation (19).

[Formula 15]

$$Z_l = \frac{8\mu}{\pi r_i^4} + j\omega \frac{\rho}{\pi r_i^2} \qquad (19)$$

(Calculation of Horizontal Impedance)

The horizontal impedance includes an omitted or branched term G and a compliance term C of the tube.

Regarding the omitted or branched term, G=0 if omission nor branching from the blood vessel wall to the peripheral tissue does not exist. If branching exists, the admittance of the branched tube is G.

Regarding the compliance term of the tube, the compliance in which the thick thickness circular tube is modeled can be used. The compliance of the axial symmetric microscopic deformation of the thick thickness circular tube in a condition of constant external pressure and axial distortion is expressed with equation (20).

[Formula 16]

$$C = \frac{dA}{dP} = \frac{2\pi r_i^2(1-v)}{E} \cdot \frac{r_i^2(1-2v)+r_o^2}{r_o^2-r_i^2} \quad (20)$$

Where E is the Young's modulus of the tube wall, v is a Poisson's ratio, $r_i$ is the inner diameter of the tube, and $r_o$ is an outer diameter of the tube.

Here, the Poisson's ratio v of the blood vessel wall is typically 0.5.

The compliance in which the thin thickness circular tube is modeled can be used in place of the compliance in which the thick thickness circular tube is modeled shown in equation (20). The compliance of the axial symmetric microscopic deformation of the thin thickness circular tube in a condition of constant external pressure and axial distortion is expressed with equation (21).

[Formula 17]

$$C = \frac{dA}{dP} = \frac{2\pi r_i^3(1-v^2)}{Eh} \quad (21)$$

Where h is the thickness of the tube wall.
(Circulatory System Model)

The circulatory system model used in the blood vessel state evaluation device 100 according to the first embodiment of the present invention divides the blood vessel constituting the living body to a plurality of zones and models the same. A so-called "Avolio model" described in reference document 1 "Avolio, A. P, Multi-branched Model of Human Arterial System, 1980, Med. & Biol. Engng. & Comp., 18,796" is known as a representative circulatory system model, and the Avolio model is adopted as the circulatory system model in the present embodiment.

Figure 6:
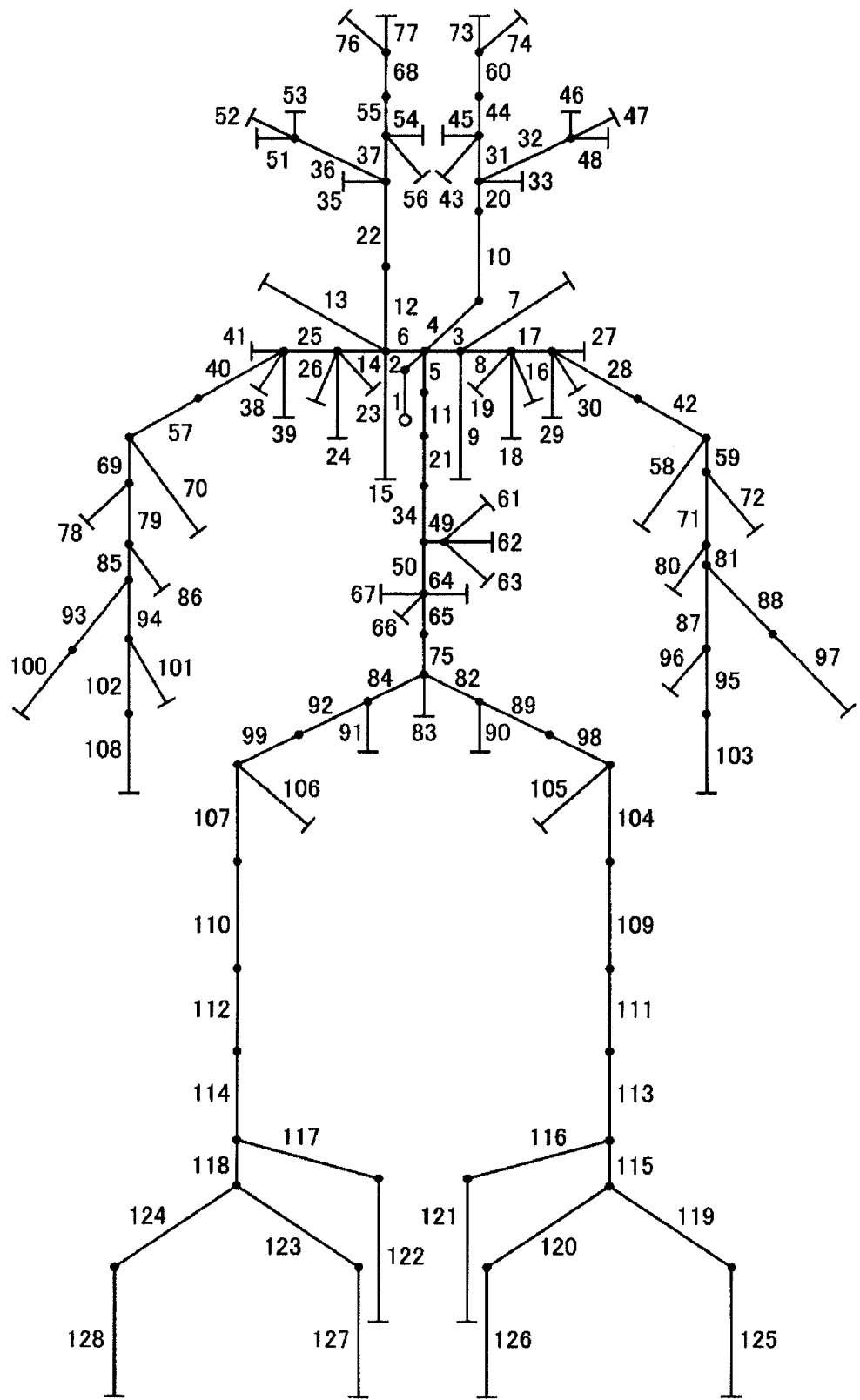
FIG. 6 is a schematic view of an Avolio model.

FIG. 6 is a schematic view of the Avolio model.

With reference to FIG. 6, in the Avolio model, the artery of the entire body is divided into 128 blood vessel elements (zones), and the shape value representing each zone is defined. Some of the shape values corresponded to each zone of the Avolio model are shown in the appendix table. The Avolio model includes length, radius, thickness of the tube wall, and the Young's modulus corresponded to each zone for the shape value. The Young's modulus in the Avolio model is a preliminary reference value, and a value in which a variable k is multiplied to the reference value is used in the fitting process described below.

The circulatory system model classifies various blood vessels constituting the living body to a plurality of sections and then models the blood vessel belonging to at least one section of the plurality of sections. Typically, the blood vessel is sectionalized to the main artery, medium-sized artery (greater than or equal to φ 3.2 mm), small artery (greater than or equal to φ 0.5 mm), arteriola (greater than or equal to φ 0.03 mm), capillary blood vessel, and the like based on the size of the blood vessel diameter in order from the blood vessel having larger blood vessel diameter. The Avolio model models the blood vessels sectionalized to the large artery and the middle-sized artery of such sections.

The method of sectionalizing the blood vessel is not limited to being based on the blood vessel diameter, and the blood vessel may be sectionalized based on a different index.

The transfer function calculating unit 36 (FIG. 2) calculates the vertical impedance and the horizontal impedance of each zone according to equation (17) and equation (20) with reference to the circulatory system model stored in advance in the storage unit 34 (FIG. 2). Furthermore, the transfer function calculating unit 36 uses the calculated vertical impedance and the horizontal impedance to calculate the transfer matrix of each zone according to equation (12), equation (13), and equation (14), and connects in cascade and/or connects in parallel each transfer function in correspondence to the actual connection relationship of each zone to calculate the pulse wave propagation model (transfer function) for the entire body with the heart as the reference point. More specifically, the 2×2 transfer matrix shown in equation (14) is sequentially connected according to the connection relationship (continuous, branched, terminating end and the like) of each zone.

The transfer function calculating unit 36 calculates the transfer functions Ga(f) and Gb(f) corresponding to the blood vessel passages to two measurement sites of the calculated pulse wave propagation model (transfer function) for the entire body. At the terminating end portion, the restriction of equation (15) is added according to the reflectivity.

The pressure (pressure $P_s$) discharged from the heart and the volumetric flow rate (volumetric flow rate $Q_s$) are unknown, but in the present embodiment, the unknowns can cancel each other out, even if present, as the target value can be obtained by calculating the phase difference characteristics between the transfer function Ga(f) and the transfer function Gb(f).

(Peripheral Part Model)

In calculating the pulse wave propagation model (transfer function) for the entire body and the transfer functions Ga(f) and Gb(f), the peripheral part model is preferably added to the Avolio model described above. This is because the Avolio model specifically provides the shape value on a relatively thick blood vessel (large artery and middle-sized artery), but only defines a constant reflectivity in which the peripheral blood vessel is simulated for the terminating end conditions. Thus, in order to obtain higher evaluation accuracy, the blood vessels (small artery, arteriola, capillary blood vessel) that are not modeled in the Avolio model are preferably taken into consideration. A configuration of adding the model (hereinafter referred to as "peripheral part model") in which the blood vessels that are not modeled in the Avolio model are modeled to the transfer matrix calculated from the Avolio model, and calculating the pulse wave propagation model (transfer function) and the like on the entire body will be described.

Such a peripheral part model is calculated using the shape difference between the shape value of the peripheral blood vessel and the shape value of the zone connected to the upstream side of the peripheral blood vessel. In the present embodiment, a difference in the total cross-sectional area of each blood vessel is representatively used for the shape difference.

Figure 7:
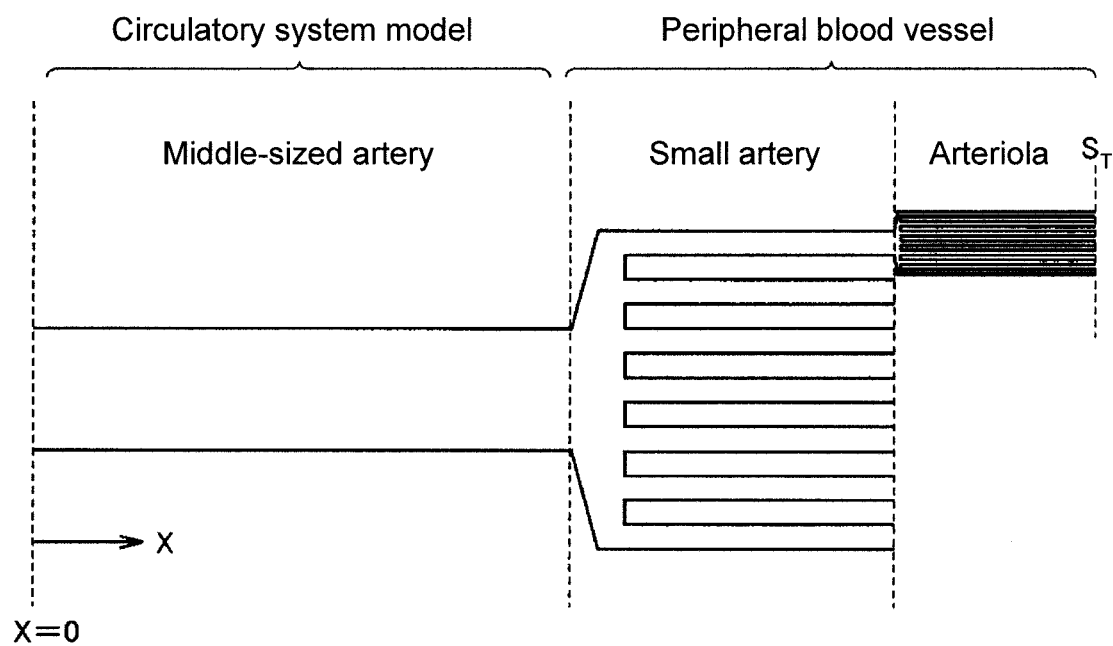
FIG. 7 is a schematic view of a peripheral part model.

FIG. 7 is a schematic view of the peripheral part model.

With reference to FIG. 7, the total cross-sectional area of each blood vessel (artery) in the entire circulatory system increases towards the thin blood vessels on the downstream after being branched. In particular, the increase rate of the total cross-sectional area of the blood vessel involved in the branching from the middle-sized artery to the arteriola is reported to be about 20 times according to reference document 2 "William F. Ganong, Review of Medical Physiology 15ed.".

In the present embodiment, the small artery and the arteriola are targets of the peripheral part model. By way of example, the increase rate of the total cross-sectional area of the blood vessel involved in branching is assumed as four times from the middle-sized artery to the small artery and five times from the small artery to the arteriola, where the lengths of the small artery and the arteriola are 10 cm and 5 cm, respectively. The general values described in reference document 2 are used for the blood vessel diameters of the small artery and the arteriola, and the thickness of the respective blood vessel wall is determined according to the ratio of the blood vessel diameter of the middle-sized artery connected to the upstream and the thickness of the blood vessel wall. Furthermore, the value same as the Young's modulus of the middle-sized artery connected to the upstream is used for the Young's modulus of the small artery and the arteriola.

For instance, the radial artery (zone number 88 or 93 of Avolio model shown in FIG. 6) and the shape value of the peripheral part model to be added thereto are shown in the following table.

TABLE 1

|  | Middle-sized artery | Small artery | Arteriola |
|---|---|---|---|
| Inner diameter of blood vessel (mm) | 3.2 | 0.50 | 0.030 |
| Outer diameter of blood vessel (mm) | 4.1 | 0.63 | 0.038 |
| Length of blood vessel (mm) | 117 | 100 | 50 |
| Young's modulus (MPa) | 0.8 | 0.8 | 0.8 |
| Total cross-sectional area ratio | 1 | 4 | 20 |
| Bessel number | 1 | 164 | 1389 |

(Terminating End Condition of Peripheral Part Model)

The terminating end condition of the arteriola in the peripheral part model described above can be arbitrarily set as described below. This is because the reflectivity (hereinafter referred to as peripheral reflectivity) at the terminating end of the middle-sized artery constituted by peripheral blood vessels does not depend on the terminating end conditions of the arteriola. Thus, in the present embodiment, the pulse wave propagation model (transfer function) and the like on the entire body are calculated with the terminating end in the peripheral part model under a non-reflection condition.

Figure 8:
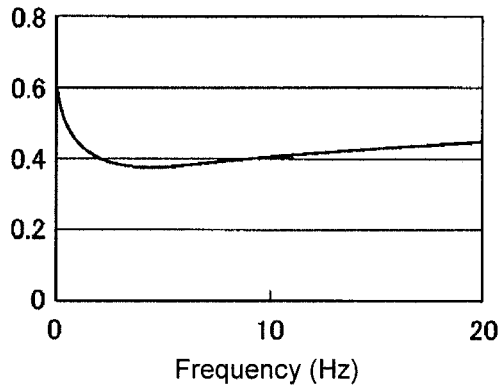
FIG. 8 is a view showing a change in peripheral reflectivity of when reflectivity $S_T$ at a terminating end of an arteriola shown in FIG. 7 is changed using a shape value shown in table 1.
Figure 8:
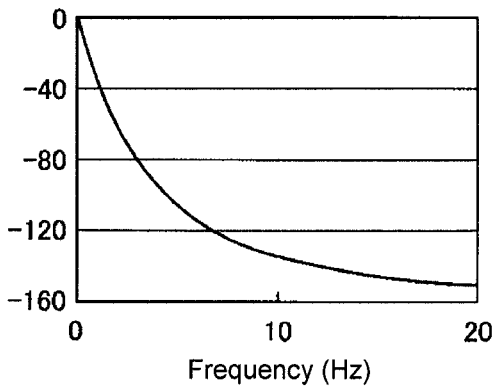
Figure 8:
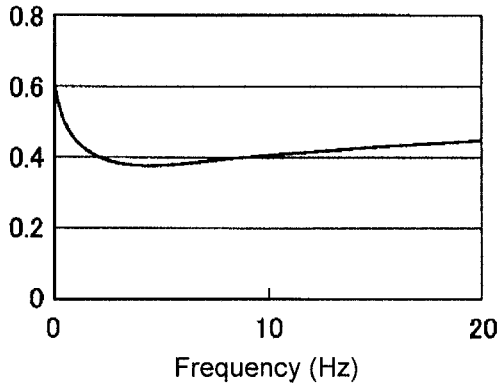
Figure 8:
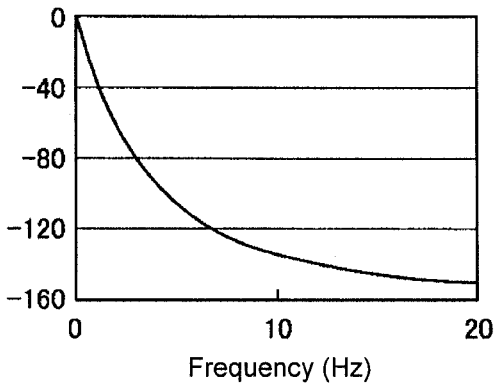
Figure 8:
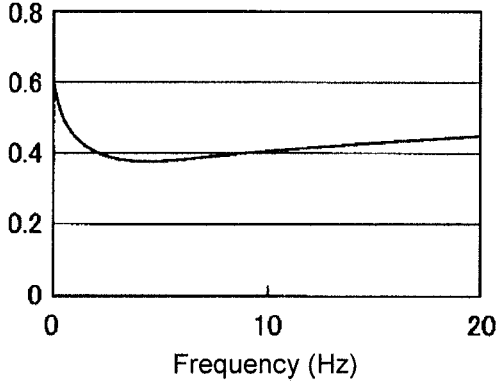
Figure 8:
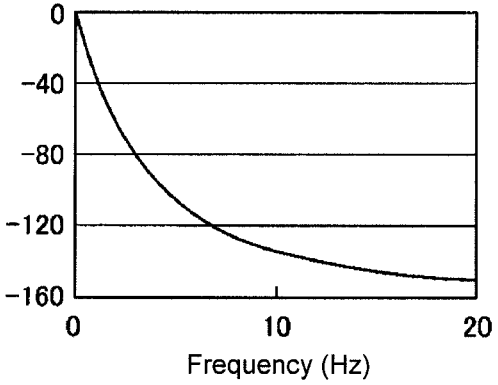

FIG. 8 is a view showing a change in peripheral reflectivity of when the reflectivity $S_T$ at the terminating end of the arteriola shown in FIG. 7 is changed using the shape value shown in table 1.

FIG. 8(a) shows a case of reflectivity $S_T=0$ (non-reflection), FIG. 8(b) shows a case of reflectivity $S_{T=1}$ (closed end), and FIG. 8(c) shows a case of reflectivity $S_T=-1$ (open end).

With reference to FIGS. 8(a) to 8(c), it can be seen that substantially the same behavior is shown in both the amplitude characteristics and the frequency characteristics irrespective of the reflectivity $S_T$ at the terminating end of the arteriola. In other words, the terminating end condition of the arteriola does not contribute to the peripheral reflectivity.

The propagation aspect of the pulse wave in each artery will be described to physically interpret such a phenomenon.

Figure 9:
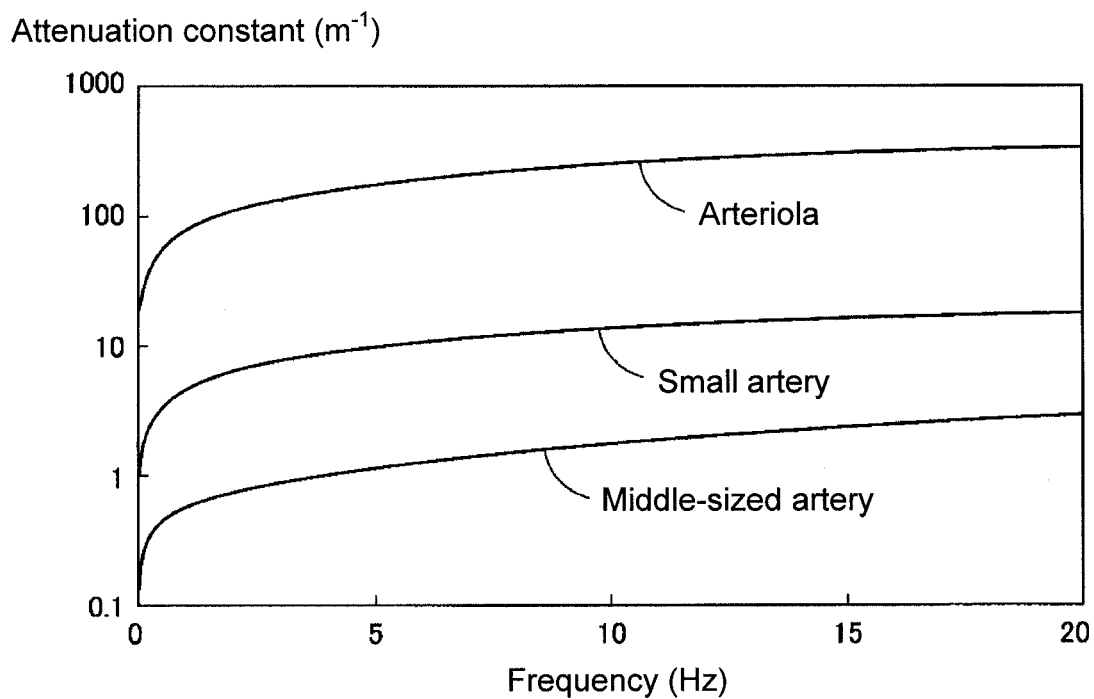
FIG. 9 is a view showing results of obtaining an attenuation constant of a pulse wave propagating through a middle-sized artery, a small artery, and an arteriola through numerical calculation.

FIG. 9 is a view showing the results of obtaining the attenuation constant of the pulse wave propagating through the middle-sized artery, the small artery, and the arteriola through numerical calculation.

With reference to FIG. 9, it can be seen that the attenuation constant exponentially increases as the tube diameter of the blood vessel through which the pulse wave propagates becomes smaller. This is assumed to be because the influence of the tube wall friction resistance of the pulse wave (fluid) is large in the thin tube. In other words, the amplitude of the pulse wave reaching the terminating end of the arteriola is extremely small compared to the amplitude of the pulse wave propagating through the middle-sized artery, and the reflected wave from the terminating end of the arteriola is assumed to be sufficiently attenuated.

Figure 10:
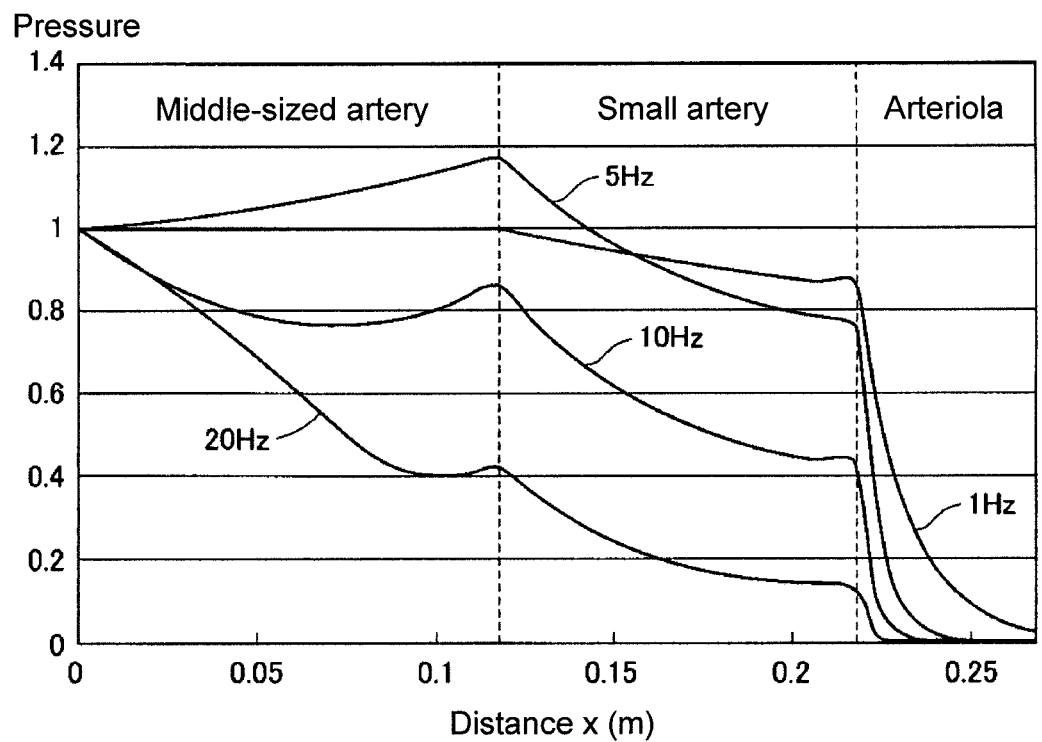
FIG. 10 is a view showing an intravascular pressure distribution of when vibrated (pressurized) at a predetermined frequency from a starting end (coordinate x) of the middle-sized artery shown in FIG. 7.

FIG. 10 is a view showing the intravascular pressure distribution of when vibrated (pressurized) at a predetermined frequency from the starting end (coordinate x) of the middle-sized artery shown in FIG. 7. In the coordinate system of FIG. 10, the starting end of the middle-sized artery shown in FIG. 7 is an origin (x=0), and a downstream direction is a positive direction of x.

FIG. 10 shows the result for four types of vibration frequencies f, 1 Hz, 5 Hz, 10 Hz, and 20 Hz. As is apparent from FIG. 10, in all vibration frequencies, the pulse wave propagating through the arteriola is sufficiently attenuated at the vicinity of the terminating end. This is because the distance attenuation of the pulse wave in the arteriola is large.

Therefore, the reflected wave from the terminating end of the arteriola is assumed to not influence the circulatory system of the upstream regardless of what kind of boundary conditions are provided on the terminating end of the arteriola. In other words, the peripheral reflectivity is determined only by the shape value of the peripheral blood vessel without being dependent on the boundary conditions of the terminating end in the peripheral part model.

(Phase Difference Characteristics)

Figure 11:
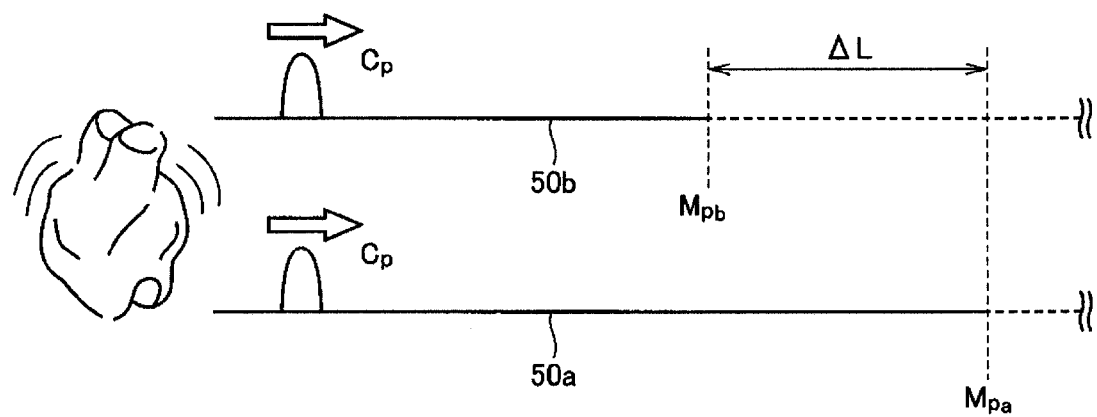
FIG. 11 is a schematic view showing a state of the pulse wave propagation in a uniform tube path.

FIG. 11 is a schematic view showing a state of the pulse wave propagation in a uniform tube path.

With reference to FIG. 11, assume that the reflected wave does not exist, and the pulse wave velocity $C_p$ is a constant not dependent on the frequency given by equation (1). The phase delay $\phi$ of the pulse wave of the measurement site $M_{pa}$ on the measurement site $M_{pb}$ is expressed with equation (22).

[Formula 18]

$$\phi = -360 \times \frac{\Delta L}{\lambda} \qquad (22)$$

Where L is a passage difference between measurement points.

Rewriting equation (22) using the pulse wave velocity $C_p$ and the frequency f, equation (23) is obtained.

[Formula 19]

$$\phi = -360 \times \frac{\Delta L}{C_p} f \qquad (23)$$

It can be seen from equation (22) that the phase diagram (phase difference characteristics) between the measurement site $M_{pa}$-measurement site $M_{pb}$ is a linear function of the frequency f, and the slope is a value corresponding to the pulse wave velocity $C_p$. Furthermore, equation (24) is obtained using equation (1) and equation (23).

[Formula 20]

$$\phi = -360 \times \sqrt{\frac{2r\rho\Delta L^2}{Eh}} f \quad (24)$$

It can be seen from equation (24) that the slope of the phase diagram becomes gradual the larger the Young's modulus E of the blood vessel wall.

(Fitting)

Referring to FIG. 2 again, where the search unit 40 fits the model such that the slope of the linear function matches the actual measurement value since the phase difference characteristics between two measurement sites is the linear function for the frequency f as mentioned above.

More specifically, the transfer function calculating unit 36 calculates the transfer functions Ga(f) and Gb(f) using a tentative Young's modulus k·$E_n$ obtained by multiplying a variable k to the Young's modulus $E_n$ (n=1 to 128) of each zone in the Avolio model. The search unit 40 optimizes the variable k such that the deviation $\Delta$ (=|$g_{exp}$–g(k)|) of the slope $g_{exp}$ of the phase line calculated by the phase line tilt calculating unit (actual measurement) 32 and the slope g(k) of the phase line calculated by the phase line tilt calculating unit (model) 38 is minimized. The optimization process is performed using a typical mathematical programming method (e.g., least square method), but the detailed description thereof will not be made since the mathematical programming method is known.

(Calculation of Phase Difference Characteristics of Actual Measurement)

The result of actually performing the measurement on two subjects 200a and 200b using the blood vessel state evaluation device 100 according to the present embodiment is shown below.

Figure 12:
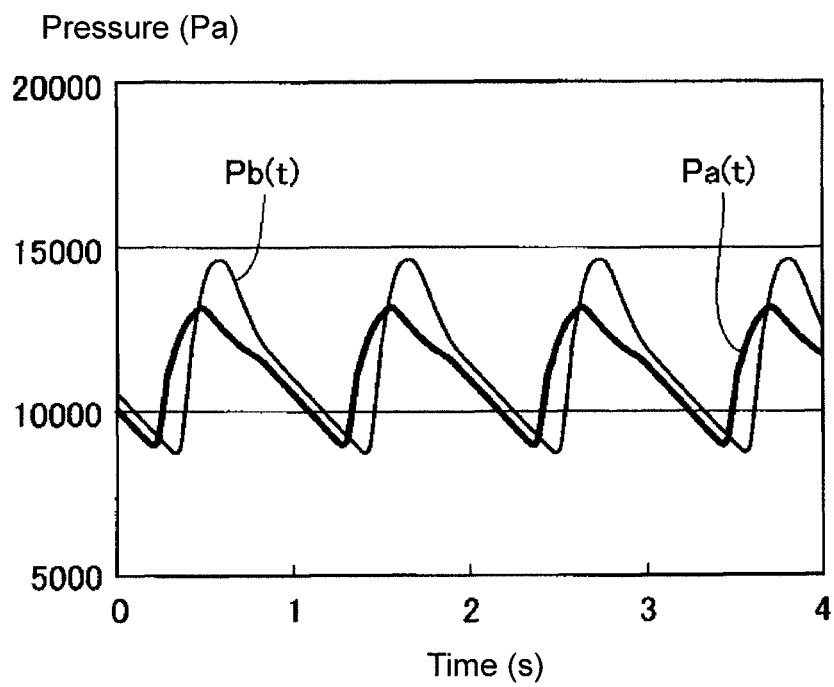
FIG. 12(a) is a view showing a time waveform of a pressure measured by attaching a pressing cuff to an upper arm and an ankle joint of a subject.
FIG. 12(b) is a view showing a time waveform of a pressure measured by attaching a pressing cuff to an upper arm and an ankle joint of a subject.
Figure 12:
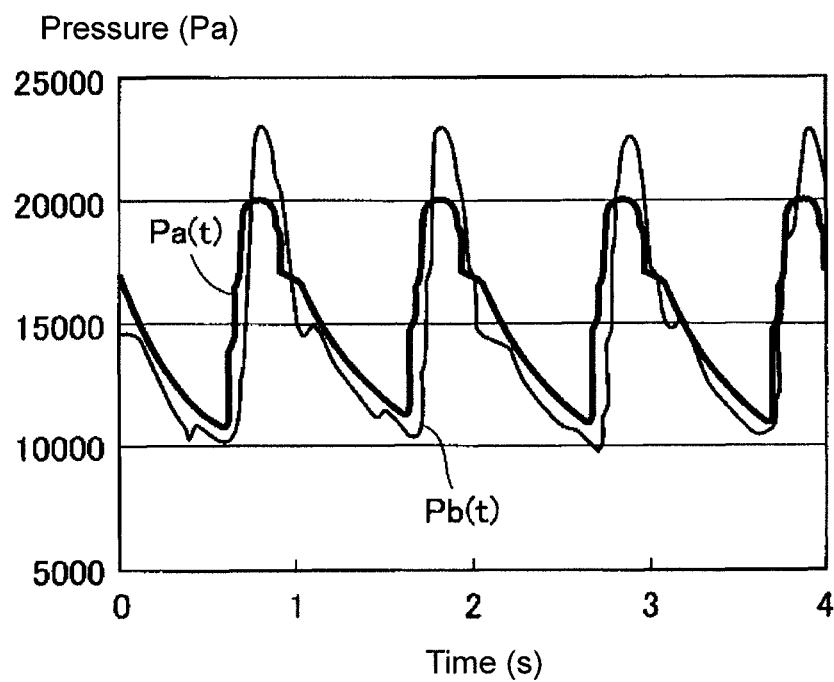

FIG. 12 is a view showing the time waveform of the pressure measured by attaching the pressing cuff to the upper arm and the ankle joint of the subjects 200a, 200b. The measurement signal Pa(t) indicates the pressure at the ankle joint, and the measurement signal Pb(t) indicates the pressure at the upper arm.

Figure 13:
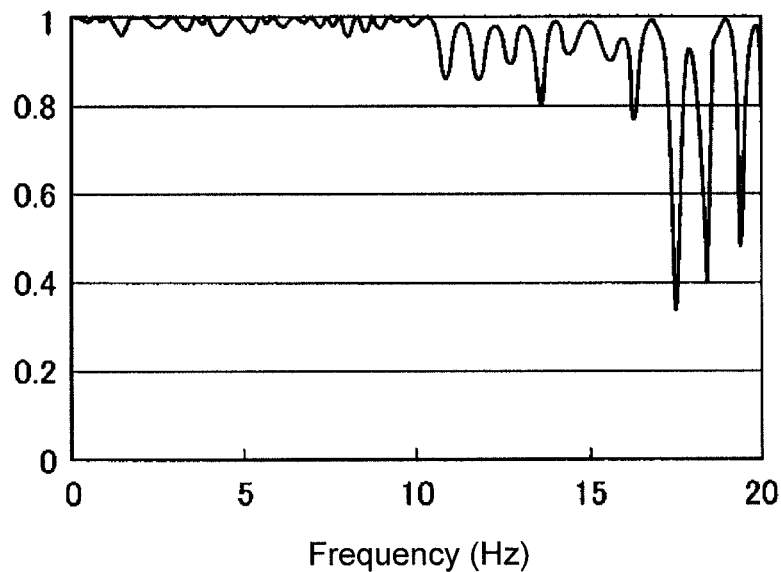
FIG. 13(a) is a view showing coherence between the pressure waveform of the upper arm and the pressure waveform of the ankle joint shown in FIG. 12(a).
FIG. 13(b) is a view showing coherence between the pressure waveform of the upper arm and the pressure waveform of the ankle joint shown in FIG. 12(b).
Figure 13:
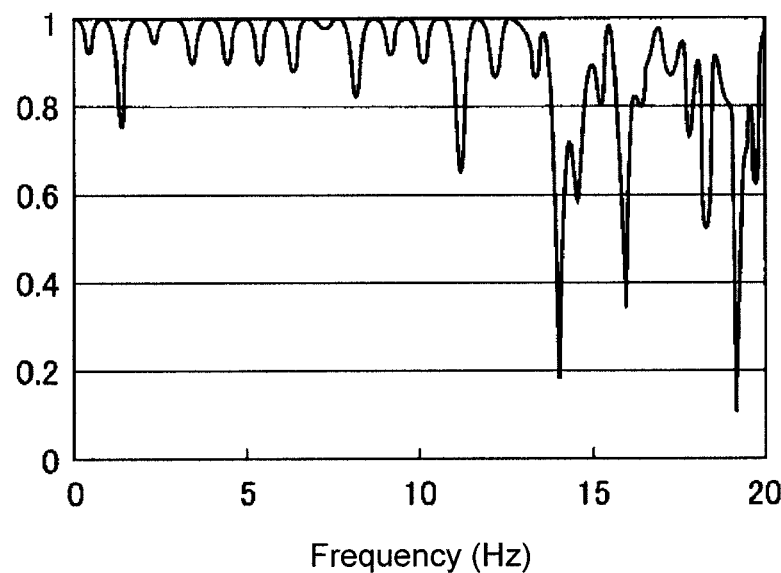

FIG. 13 is a view showing coherence between the pressure waveform of the upper arm and the pressure waveform of the ankle joint shown in FIG. 12.

FIGS. 12(a) and 13(a) show the measurement result of the subject 200a, and FIGS. 12(b) and 13(b) show the measurement result of the subject 200b.

Here, the coherence is the index indicating the correlation at the frequency region between the waveforms, where the correlation of the waveforms is higher the larger the coherence (closer to one). The coherence shown in FIG. 13 is calculated according to equation (25).

[Formula 21]

$$C_{b\_a}(\omega) = \frac{|X_{b\_a}(\omega)|^2}{X_{b\_b}(\omega)X_{a\_a}(\omega)} \quad (25)$$

$X_{b\_b}(\omega)$ is a power spectrum of $P_b(t)$
$X_{a\_a}(\omega)$ is a power spectrum of $P_a(t)$
$X_{b\_a}(\omega)$ is a power spectrum of $P_b(t)$ and $P_a(t)$ As shown in FIGS. 13(a) and 13(b), it can be seen that the coherence is low at a specific frequency. Various dynamic factors for such lowering in coherence can be considered, and typically, the fact that nonlinearity of the human body or the pressure at the measurement site becomes a node in the specific frequency is assumed to be influencing. The coherence is also assumed to decrease due to artificial factors such as a posture and slight movement of the subject during the measurement.

Such data of low coherence may increase the error in analysis, and thus the data in which the coherence between the measurement signal Pa(t) and the measurement signal Pb(t) is smaller than a predefined threshold value (e.g., 0.7) is desirably excluded. Thus, the phase line tilt calculating unit (actual measurement) 32 (FIG. 2) calculates the slope $g_{exp}$ of the phase line using only the frequency component in which the coherence between the measurement signal Pa(t) and the measurement signal Pb(t) is higher than the predefined threshold value.

Figure 14:
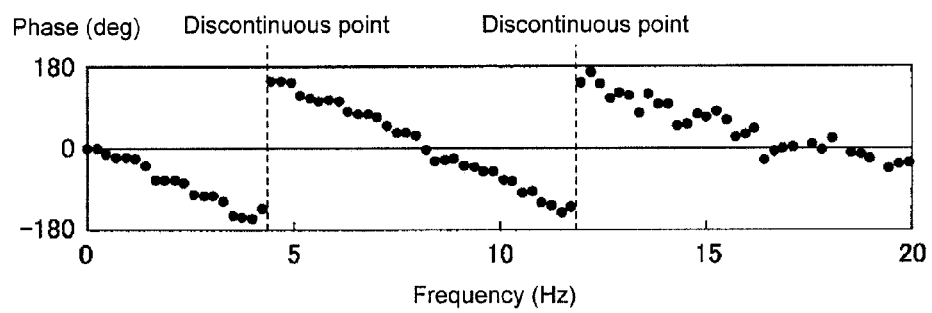
FIG. 14(a) is a phase line diagram in which a phase difference on each frequency component between a measurement signal Pa(t) and a measurement signal Pb(t) shown in FIG. 12(a) are plotted.
FIG. 14(b) is a phase line diagram in which a phase difference on each frequency component between a measurement signal Pa(t) and a measurement signal Pb(t) shown in FIG. 12(b) are plotted.
Figure 14:
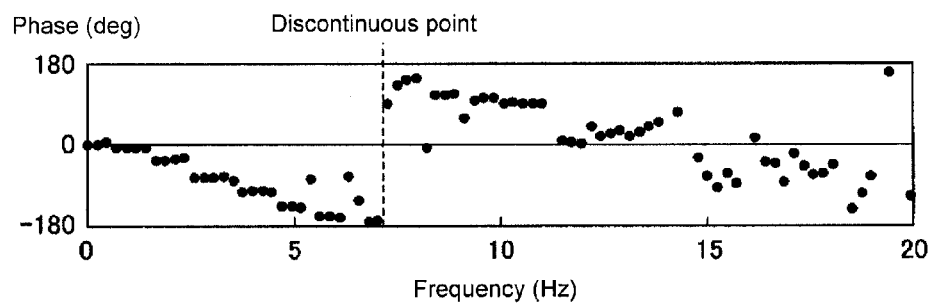

FIG. 14 is a phase line diagram in which the phase difference on each frequency component between the measurement signal Pa(t) and the measurement signal Pb(t) shown in FIG. 12 are plotted. FIG. 14(a) shows the phase line diagram corresponding to FIG. 12(a), and FIG. 14(b) shows the phase line diagram corresponding to FIG. 12(b). In FIGS. 14(a) and 14(b), data in which the coherence is lower than "0.7" is excluded.

With reference to FIGS. 14(a) and 14(b), each phase line diagram has discontinuous points with ±180° as a boundary. This means that the phase difference of greater than or equal to one period (360° is created at the frequency component of greater than or equal to the predetermined frequency. The phase line tilt calculating unit (actual measurement) 32 performs correction in units (n×360° corresponding to one or more periods with respect to the discontinuous points on the phase line diagram to calculate the phase difference characteristics of the actual measurement.

Figure 15:
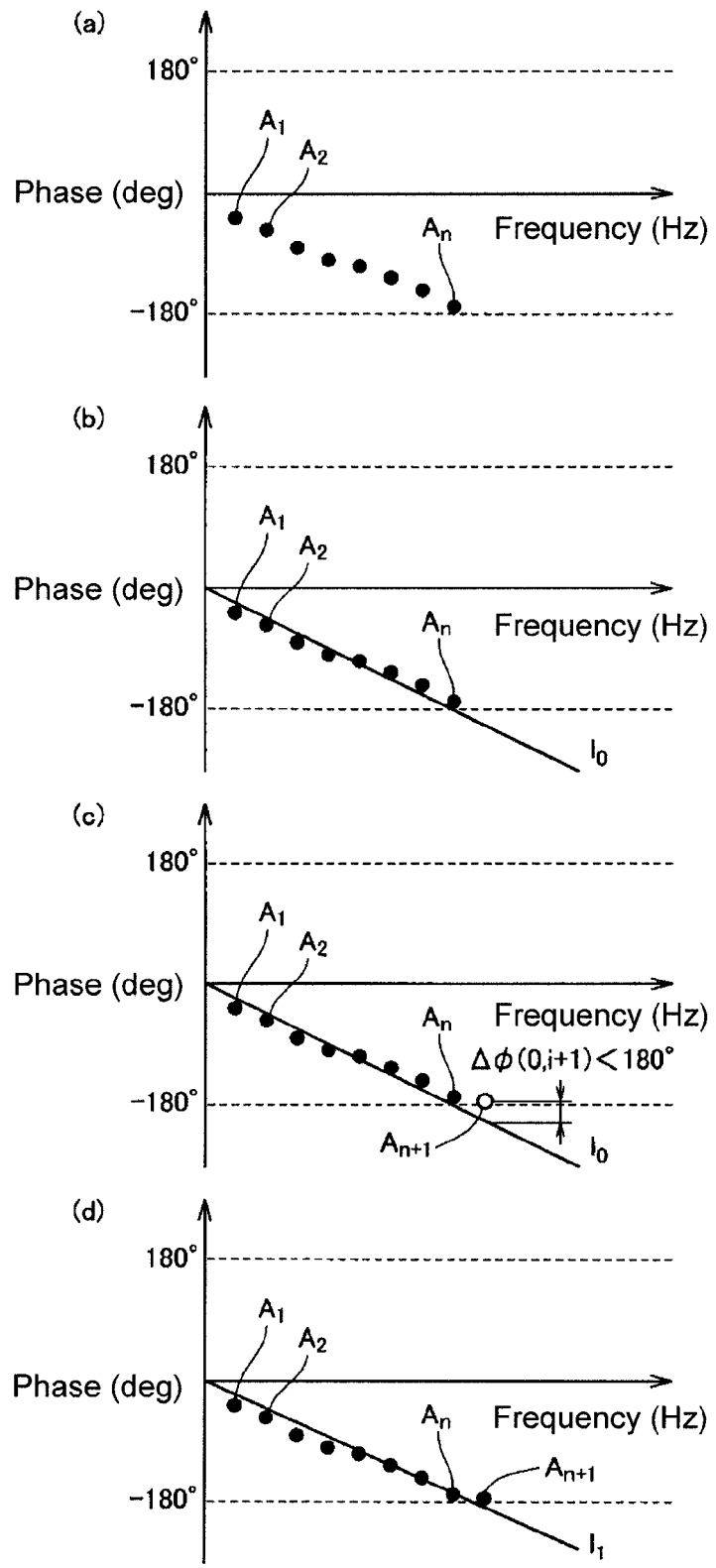
FIG. 15(a) is a schematic view for describing a correction process of the phase line diagram performed by a phase line tilt calculating unit (actual measurement).
FIG. 15(b) is a schematic view for describing a correction process of the phase line diagram performed by a phase line tilt calculating unit (actual measurement).
FIG. 15(c) is a schematic view for describing a correction process of the phase line diagram performed by a phase line tilt calculating unit (actual measurement).
FIG. 15(d) is a schematic view for describing a correction process of the phase line diagram performed by a phase line tilt calculating unit (actual measurement).
Figure 16:
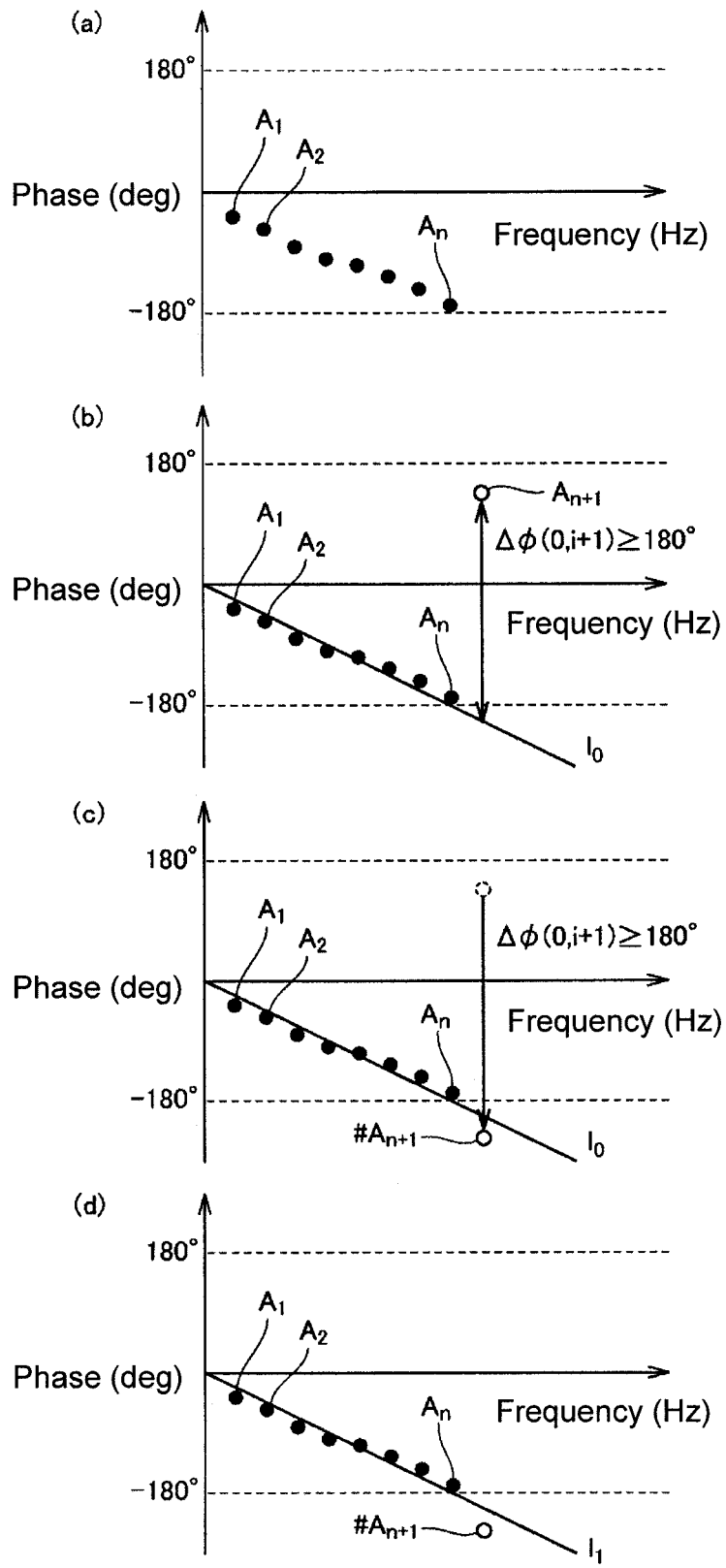
FIG. 16(a) is a schematic view for describing the correction process of the phase line diagram performed by the phase line tilt calculating unit (actual measurement).
FIG. 16(b) is a schematic view for describing the correction process of the phase line diagram performed by the phase line tilt calculating unit (actual measurement).
FIG. 16(c) is a schematic view for describing the correction process of the phase line diagram performed by the phase line tilt calculating unit (actual measurement).
FIG. 16(d) is a schematic view for describing the correction process of the phase line diagram performed by the phase line tilt calculating unit (actual measurement).

FIGS. 15 and 16 are schematic views for describing the correction process of the phase line diagram performed by the phase line tilt calculating unit (actual measurement) 32.

With reference to FIG. 15(a), the phase characteristics Pa(f) obtained by frequency converting the measurement signal Pa(T) and the phase characteristics Pb(f) obtained by frequency converting the measurement signal Pa(t) are compared, and the phase difference $A_i$ corresponding to the frequency $f_i$ is plotted on the phase line diagram. The frequency $f_i$ is the $i^{th}$ frequency component counting from the low frequency side. An initial regression line $l_0$ is calculated using n phase differences $\{A_1, A_2, \ldots, A_n\}$ of a range in which the discontinuous points do not exist of the phase difference $A_i$ plotted on the phase line diagram (FIG. 15(b)).

The n+1$^{th}$ phase difference $A_{n+1}$ and the phase corresponding to the frequency $f_{n+1}$ of the initial regression line $l_0$ are then compared. As shown in FIG. 15(c), if the deviation $\Delta\phi$ (0, i+1) thereof is smaller than 180°, the regression line $l_1$ is calculated using the phase difference group $\{A_1, A_2, \ldots, A_n, A_{n+1}\}$ in which the n+1th phase difference $A_{n+1}$ is added to the n phase difference $\{A_1, A_2, \ldots, A_n\}$ used in the initial reference regression $l_0$ (FIG. 15(d)).

As shown in FIG. 16(c), if the deviation $\Delta\phi$ (0, i+1) is greater than or equal to 180°, determination is made that discontinuous points exist. 360°×m (m is an integer greater than or equal to one) is subtracted from the phase difference $A_{n+1}$ to transition the phase difference $A_{n+1}$ to the phase difference #$A_{n+1}$ such that the deviation with respect to the initial regression line $l_0$ becomes smaller than 180°. In other words, the apparent error of the measured data is corrected.

The regression line $l_1$ is calculated using the phase difference group $\{A_1, A_2, \ldots, A_n, \#A_{n+1}\}$ in which the corrected phase difference #$A_{n+1}$ is added to the n phase difference {$A_1$, $A_2$, ..., $A_n$} used in the calculation of the initial reference regression $l_0$ (FIG. 16(d)).

The plotting and the update of the regression line are similarly repeated for all phase differences $A_i$.

Figure 17:
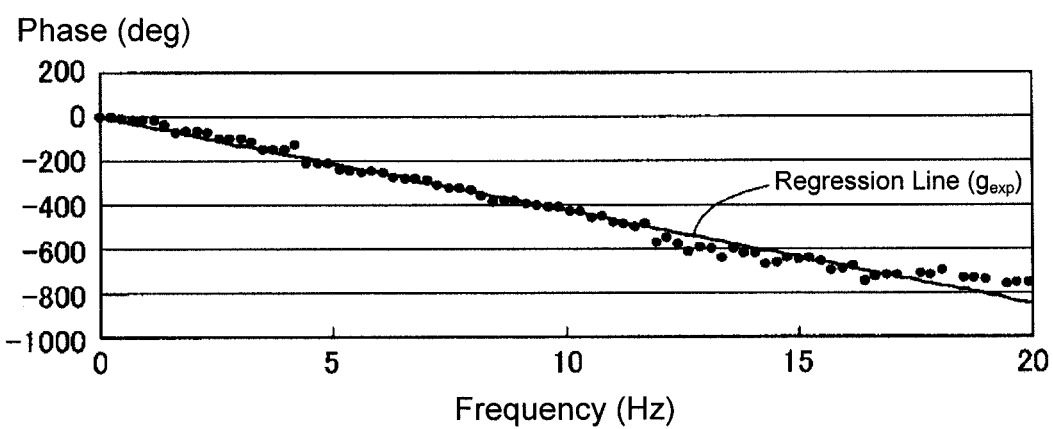
FIG. 17(a) is a view showing a result in which the phase line diagram shown in FIG. 14(a) is corrected and made continuous.
FIG. 17(b) is a view showing a result in which the phase line diagram shown in FIG. 14(b) is corrected and made continuous.
Figure 17:
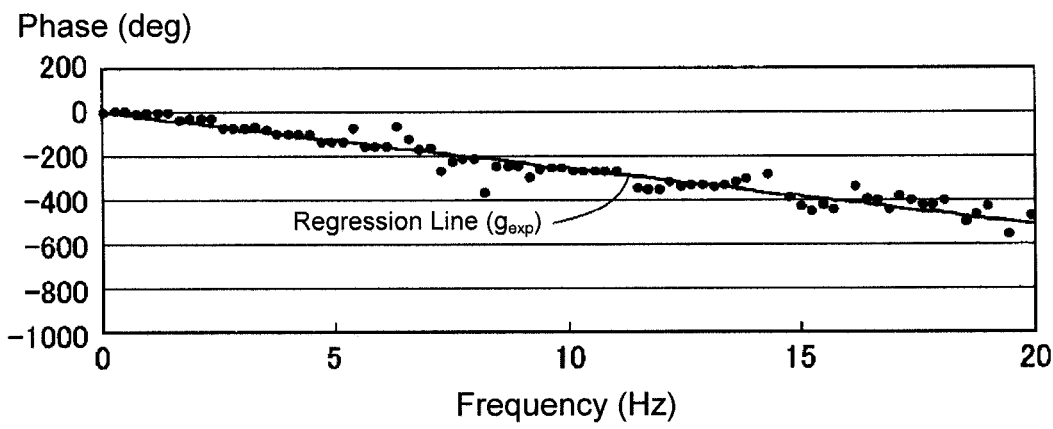

FIG. 17 is a view showing a result in which the phase line diagram shown in FIG. 14 is corrected and made continuous. FIG. 17(a) shows the phase line diagram corresponding to FIG. 14(a), and FIG. 17(b) shows the phase line diagram corresponding to FIG. 14(b).

With reference to FIGS. 17(a) and 17(b), it can be seen that each phase difference is corrected and the phase line diagram is made continuous by the above method. In FIGS. 17(a) and 17(b), the regression lines of the plotted phase data are also shown, where the slope of the regression line corresponds to the slope $g_{exp}$ shown in FIG. 2.

(Flowchart)

Figure 18:
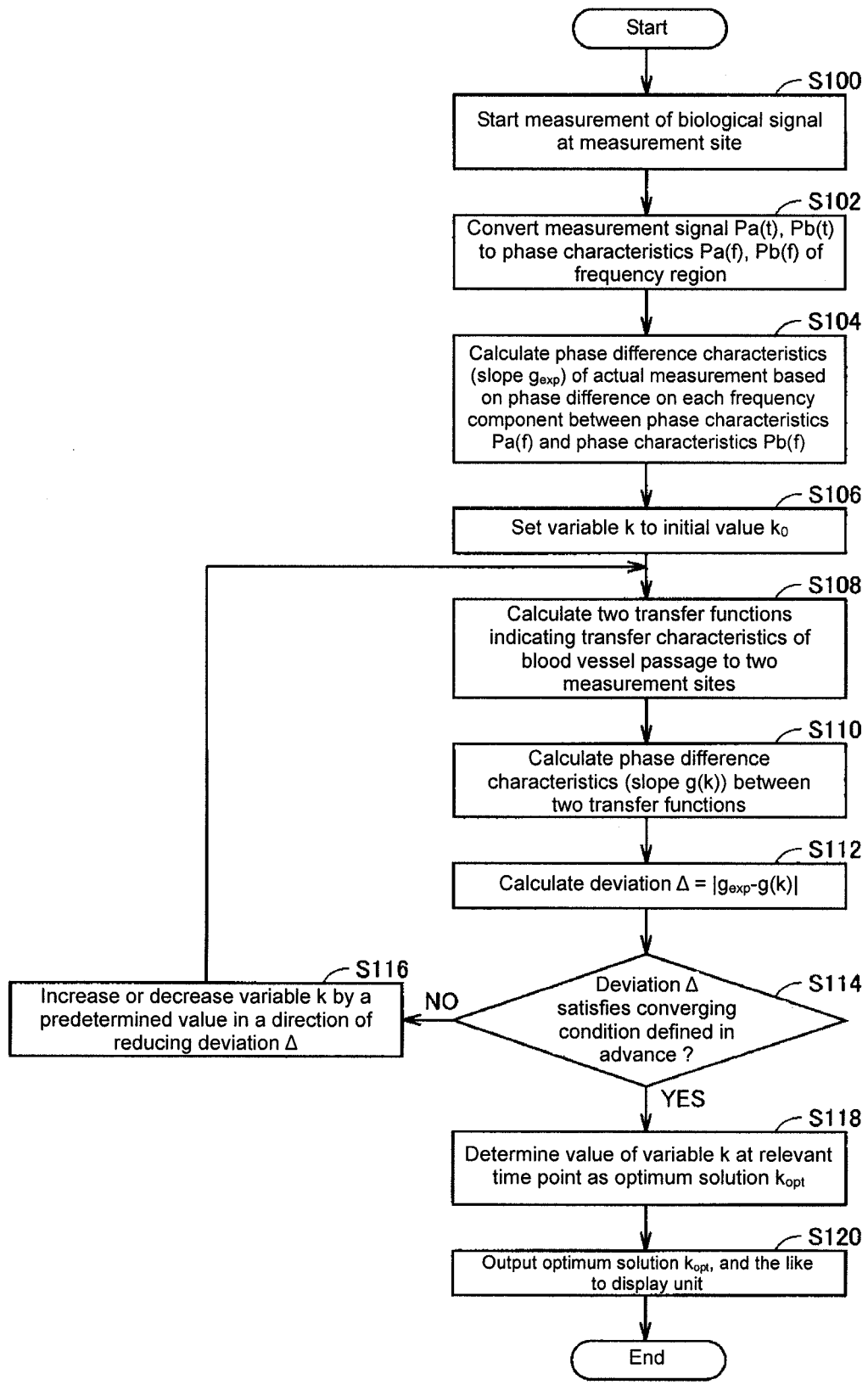
FIG. 18 is a flowchart showing procedures of the process executed in the blood vessel state evaluation device according to the first embodiment of the present invention.

FIG. 18 is a flowchart showing the procedures of the process executed in the blood vessel state evaluation device 100 according to the first embodiment of the present invention. Each process shown in the flowchart of FIG. 18 realizes each function shown in FIG. 2 by having the CPU 10 of the control unit 2 read out the program stored in advance in the ROM 12, develop the same on the RAM 13, and execute each command.

With reference to FIG. 18, the CPU 10 provides the measurement command to the measurement units 20a, 20b in response to the operation of the operation unit 6 and the like by the user, and the measurement units 20a, 20b start the measurement of the biological signal at the predetermined measurement site of the subject 200 (step S100).

The CPU 10 then converts the measurement signals Pa(t), Pb(t) or the time waveform measured in the measurement units 20a, 20b to the phase characteristics Pa(f), Pb(f) of the frequency region (step S102). The CPU 10 calculates the phase difference characteristics (slope $g_{exp}$) of the actual measurement based on the phase difference on each frequency component between the phase characteristics Pa(f) and the phase characteristics Pb(f) (step S104).

The CPU 10 sets the variable k to an initial value $k_0$ (step S106). With reference to the circulatory system model stored in the ROM 12 and the like, two transfer functions indicating the transfer characteristics of the blood vessel passages from the heart to the two measurement sites where the pressing cuffs 24a, 24b are attached are calculated (step S108). In calculating the transfer function, a value in which the variable k is multiplied to the defined reference Young's modulus in the circulatory system model is used for the Young's modulus of each zone. The CPU 10 then calculates the phase difference characteristics (slope g(k)) between the two transfer functions calculated in step S106 (step S110).

Thereafter, the CPU 10 calculates the deviation Δ (=|$g_{exp}$−g(k)|) between the phase difference characteristics (slope $g_{exp}$) of the actual measurement calculated in step S104 and the phase difference characteristics (slope g(k)) between the transfer functions calculated in step S110 (step S112). The CPU 10 then determines whether or not the deviation Δ satisfies the converging condition defined in advance (step S114). Typically, whether or not the deviation Δ is smaller than the predefined threshold value is determined.

If the deviation Δ does not satisfy the predefined converging condition (NO in step S114), the CPU 10 increases or decreases the variable k by a predetermined value in a direction of reducing the deviation Δ (step S116). The processes after step S108 are then executed again.

If the deviation Δ satisfies the predefined converging condition (YES in step S114), the CPU 10 determines the value of the variable k at the relevant time point as the optimum solution $k_{opt}$ (step S118). The CPU 10 then outputs the determined optimum solution $k_{opt}$, the Young's modulus converted using the optimum solution $k_{opt}$, the evaluation result of the optimum solution $k_{opt}$, and the like to the display unit 4 (step S120). The evaluation process is then terminated.

In the above description, a method of calculating the pulse wave propagation model (transfer function) for the entire body having the heart as the input end, the peripheral part model, and the transfer functions Ga(f), Gb(f) has been described in detail, but such models or transfer functions do not necessarily need to be calculated for every evaluation process. In other words, the models and the transfer functions calculated before the evaluation process may be stored in the storage unit 34 in advance.

According to the first embodiment of the present invention, the optimum solution of the elasticity variable k reflecting the frequency characteristics of the measurement signal of the actual measurement can be obtained. Thus, a state of the blood vessel (degree of arterial sclerosis) can be evaluated at higher accuracy in view of the frequency characteristics.

Second Embodiment

In the first embodiment of the present invention, a configuration of calculating the elasticity variable indicating the degree of elastic force of the blood vessel has been described, but it is also effective to calculate the pulse wave velocity such that the evaluation reference similar to the pulse wave velocity method put to practical use from the related art can be used. Therefore, in the second embodiment, a configuration of calculating the pulse wave velocity between two points defined in advance will be described.

The configuration of the blood vessel state evaluation device 100# according to the second embodiment of the present invention is similar to the blood vessel state evaluation device 100 according to the first embodiment of the present invention shown in FIG. 1 other than the process executed in the control unit 2#, and thus detailed description thereof will not be repeated.

Figure 19:
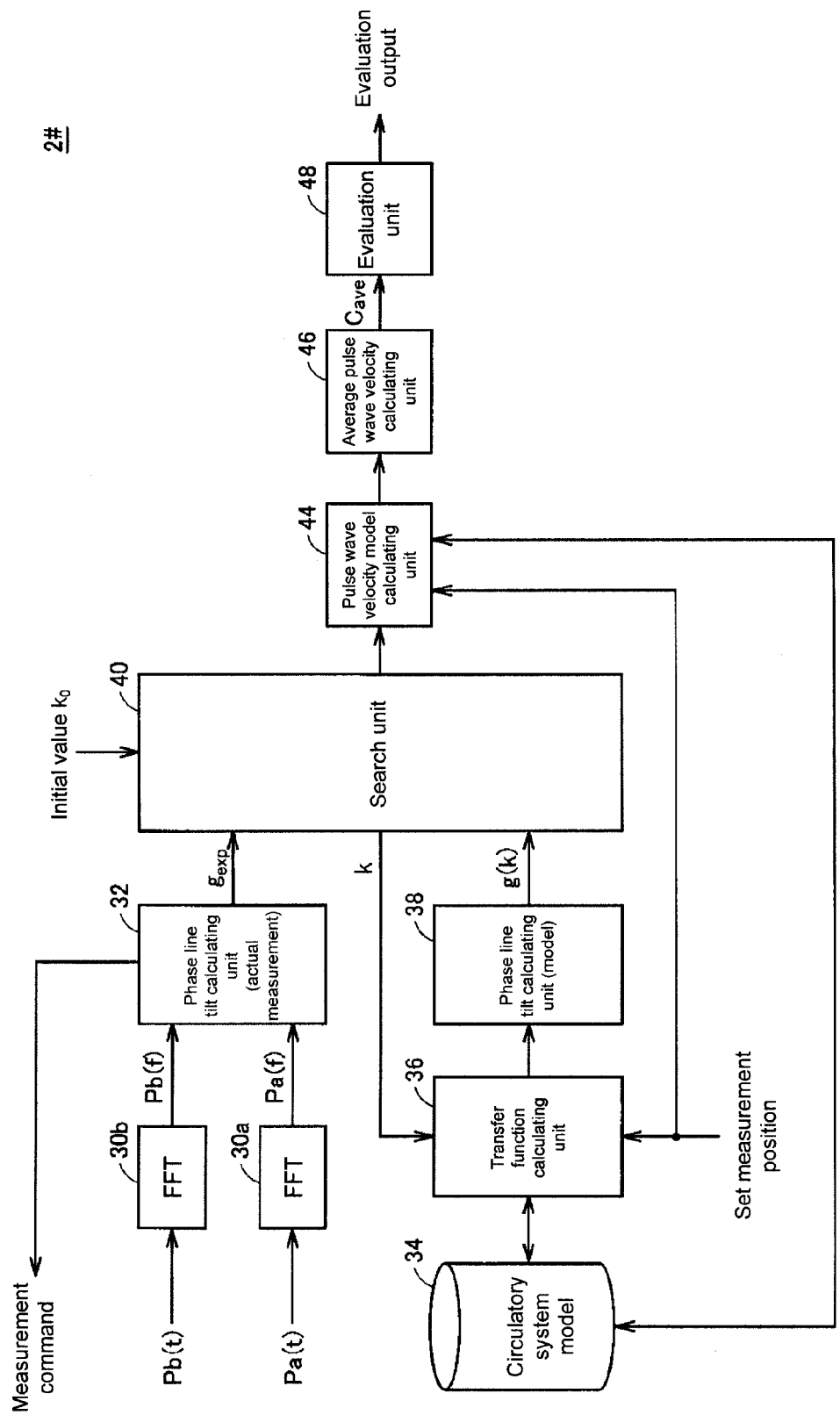
FIG. 19 is a function block diagram schematically showing a function executed in a control unit of a blood vessel state evaluation device according to a second embodiment of the present invention.

FIG. 19 is a function block diagram schematically showing the function executed in the control unit 2# of the blood vessel state evaluation device 100# according to the second embodiment of the present invention.

With reference to FIG. 19, the control unit 2# is arranged with a pulse wave velocity model calculating unit 44, an average pulse wave velocity calculating unit 46, and an evaluation unit 48 in place of the evaluation unit 42 in the function executed in the control unit 2 according to the first embodiment of the present invention shown in FIG. 2. Other functions are the same as FIG. 2, and thus detailed description thereof will not be repeated.

The pulse wave velocity model calculating unit 44 calculates a mathematical model for calculating the pulse wave velocity propagating between two points defined in advance based on the optimum solution $k_{opt}$ fitted by the search unit 40. The pulse wave velocity propagating between two point means the pulse wave velocity spatially averaged between two measurement sites. In other words, the pulse wave velocity of each zone of the above-mentioned circulatory system model changes according to the tube diameter and the tube length, and thus the pulse wave velocity increases or decreases according to the shape of the propagation passage between two measurement sites. The spatial average process described below is performed to calculate the pulse wave velocity (hereinafter also referred to as "average pulse wave velocity") between the measurement sites in order to ensure the consistency with the conventional pulse wave velocity method. The pulse wave velocity model calculating unit 44 calculates the model including such an averaging process.

The average pulse wave velocity calculating unit 46 performs calculation based on the mathematical model calculated in the pulse wave velocity model calculating unit 44, and calculates the average pulse wave velocity $C_{ave}$.

The evaluation unit 48 compares the average pulse wave velocity $C_{ave}$ calculated in the average pulse wave velocity calculating unit 46 with the reference value defined in advance, and outputs the evaluation on the degree of arterial sclerosis to the display unit 4 (FIG. 1) and the like.

(Calculation of Average Pulse Wave Velocity)

The shape value of the blood vessel in the propagation passage between two measurement sites is assumed to be known based on the circulatory system model stored in advance in the storage unit 34 and the optimum solution $k_{opt}$ fitted by the search unit 40.

Figure 20:
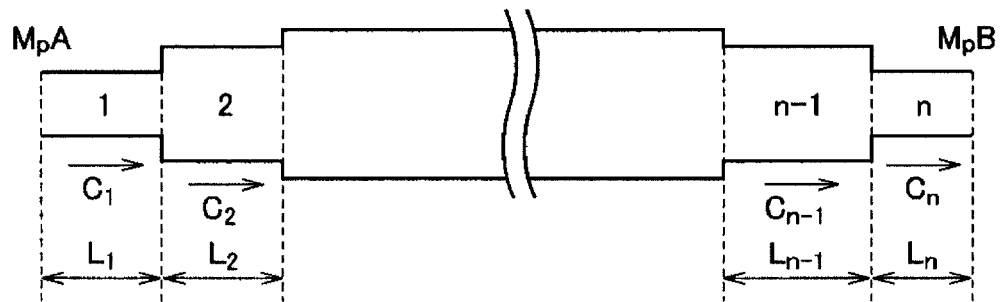
FIG. 20 is a view of a tube path model schematically showing a passage between two measurement sites MpA, MpB.

FIG. 20 is a view of a tube path model schematically showing the passage between two measurement sites MpA, MpB.

With reference to FIG. 20, n element tube paths (zone) are connected in series in the passage between two measurement sites MpA, MpB. The average pulse wave velocity between the measurement sites MpA-MpB is obtained with equation (26) where the zone length for the zone i is $L_i$, the pulse wave velocity is $C_i$, and the time necessary for the propagation of the pulse wave is $t_i$.

[Formula 22]

$$C_p = \frac{\sum_{i=1}^{n} L_i}{\sum_{i=1}^{n} t_i} \quad (26)$$

Equation (26) can be expressed as equation (27) using $t_i = L_i/C_i$.

[Formula 23]

$$C_p = \frac{\sum_{i=1}^{n} L_i}{\sum_{i=1}^{n} \left(\frac{L_i}{C_i}\right)} \quad (27)$$

The pulse wave velocity $C_i$ of each zone is expressed as equation (28) using equation (12).

[Formula 24]

$$C_i = \frac{\omega}{\operatorname{Im}(\gamma_i)} \quad (28)$$

Where $\gamma_i$ is the propagation constant in the zone i.

Therefore, the average pulse wave velocity between the measurement sites can be accurately calculated with the frequency characteristics reflected by specifically evaluating the pulse wave velocity of each zone. Furthermore, even if the pulse wave velocity of each zone differs depending on the passage, a significant value can be guaranteed as the average pulse wave velocity between the measurement sites.

Evaluation Example

Figure 21:
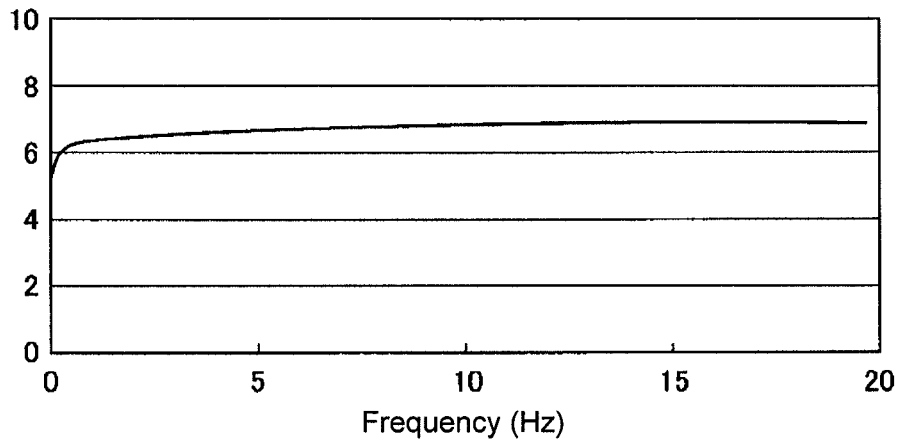
FIG. 21(a) is a view showing a result of calculating an average pulse wave velocity based on the measurement signals Pa(t), Pb(t) actually measured from a subjectshown in FIG. 12.
FIG. 21(b) is a view showing a result of calculating an average pulse wave velocity based on the measurement signals Pa(t), Pb(t) actually measured from a subjectshown in FIG. 12.
Figure 21:
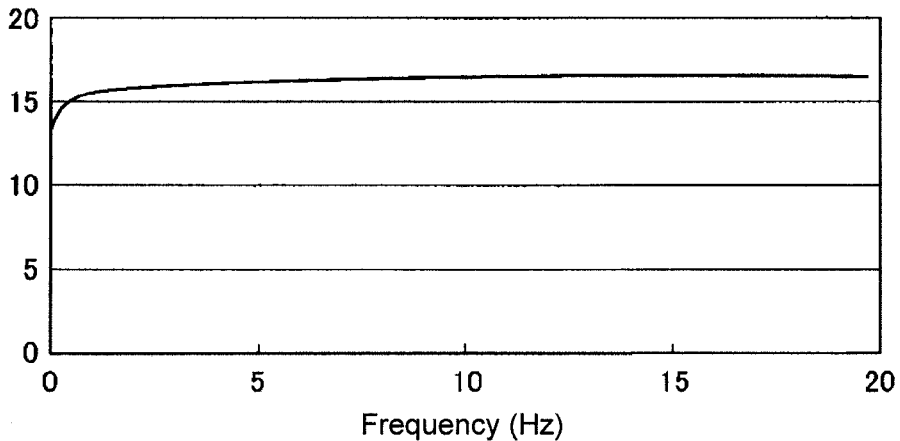

FIG. 21 is a view showing the result of calculating the average pulse wave velocity based on the measurement signals Pa(t), Pb(t) actually measured from the subjects 200a, 200b shown in FIG. 12. FIG. 21(*a*) shows the calculation result of the subject 200a, and FIG. 21(*b*) shows the calculation result of the subject 200b.

With reference to FIGS. 21(*a*) and 21(*b*), it can be seen that the average pulse wave velocity is identified with the frequency characteristics reflected for each subject 200a and 200b. Comparing the calculation results of the subjects 200a and 200b, it can be seen that the pulse wave velocity of the subject 200b is greater, and that the arterial sclerosis is relatively advancing.

Figure 22:
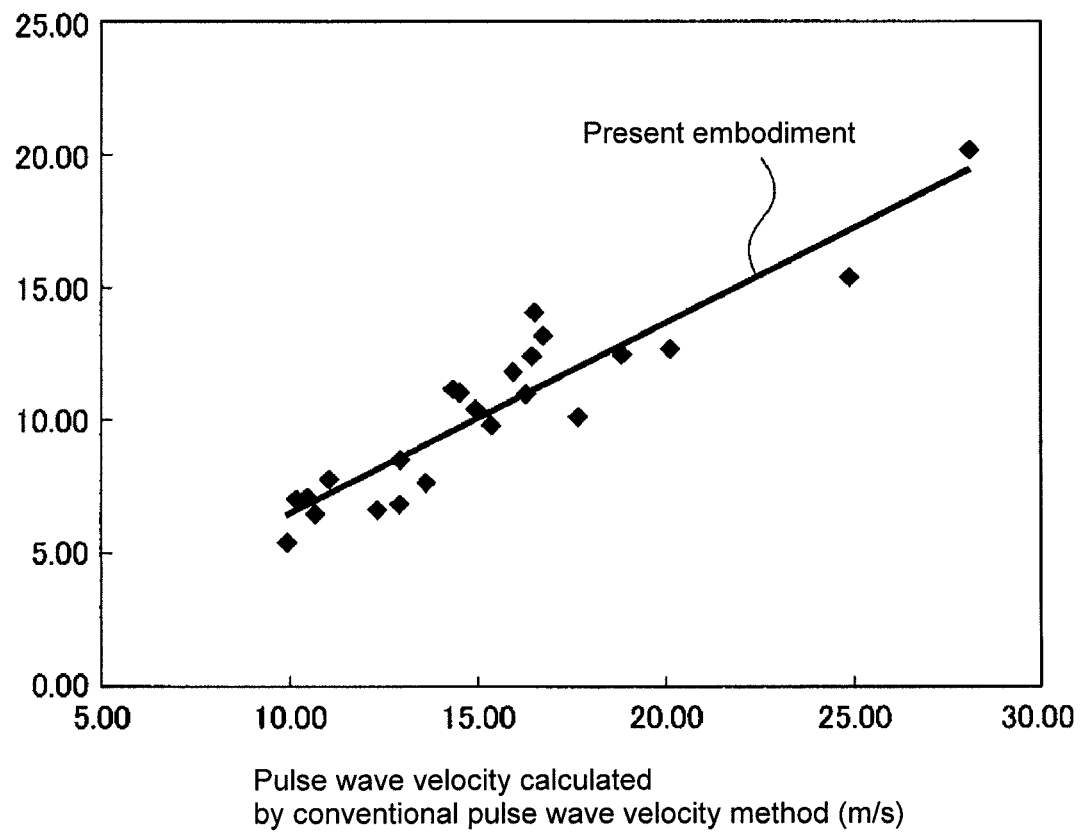
FIG. 22 is a view comparing the calculation result by the blood vessel state evaluation method according to the second embodiment of the present invention and a measurement result obtained through a conventional pulse wave velocity method (baPWV method).

FIG. 22 is a view comparing the calculation result by the blood vessel state evaluation method according to the second embodiment of the present invention with the measurement result obtained through the conventional pulse wave velocity method (baPWV method). FIG. 22 shows the result having 23 subjects as targets. As described above, the pulse wave velocity $C_i$ of each zone has frequency dependency, and thus the pulse wave velocity $C_i$ corresponding to the frequency corresponding to the pulsating period of each measurement body, and the average pulse wave velocity $C_{ave}$ are used.

With reference to FIG. 22, the correlation coefficient of the calculation result by the blood vessel state evaluation method according to the second embodiment of the present invention and the measurement result obtained by the conventional pulse wave velocity method is 0.93. From this result, the blood vessel state evaluation method according to the present embodiment has a relatively high correlation with the measurement result by the conventional pulse wave velocity method, and can evaluate the degree of arterial sclerosis using the evaluation reference similar to the evaluation reference accumulated by the pulse wave velocity method.

(Flowchart)

Figure 23:
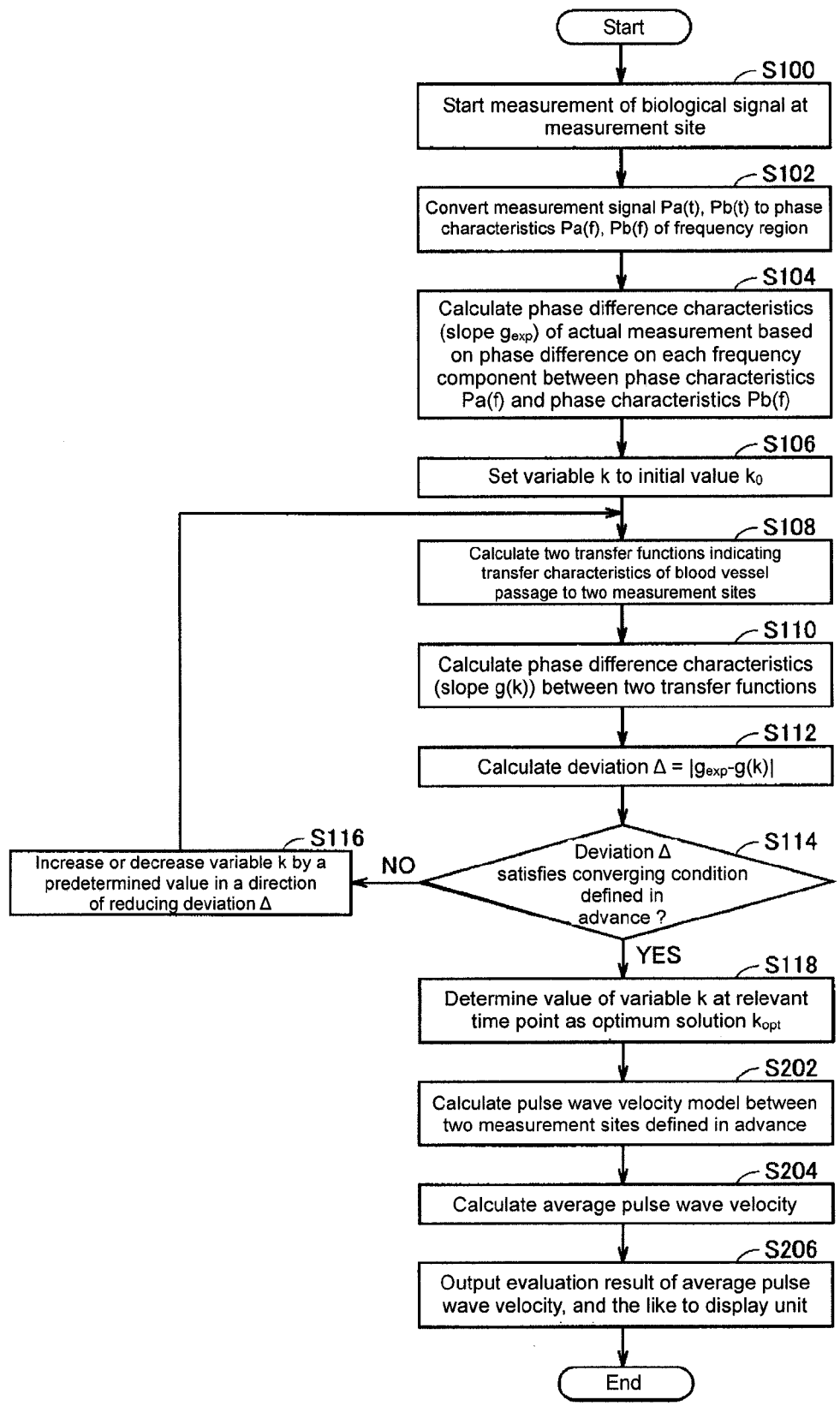
FIG. 23 is a flowchart showing a procedure of processes executed in the blood vessel state evaluation device according to the second embodiment.

FIG. 23 is a flowchart showing a procedure of the processes executed in the blood vessel state evaluation device 100# according to the second embodiment. Each process shown in the flowchart of FIG. 23 realizes each function shown in FIG. 19 by having the CPU 10 of the control unit 2# read out the program stored in advance in the ROM 12, develop the same on the RAM 13, and execute each command.

With reference to FIG. 23, the CPU 10 first executes processes similar to step S100 to step S118 shown in FIG. 18. Such processes are similar to FIG. 18, and thus detailed description thereof will not be repeated.

The CPU 10 calculates the pulse wave velocity model between two measurement sites defined in advance based on the optimum solution $k_{opt}$ determined in step S118 and the shape value of the circulatory system model stored in the ROM 12 and the like (step S202). The CPU 10 also calculates the average pulse wave velocity according to the calculated pulse wave velocity model (step S204).

The CPU 10 then outputs the evaluation result of the average pulse wave velocity calculated in step S204, and the like to the display unit 4 (step S206). The evaluation process is then terminated.

According to the second embodiment of the present invention, the average pulse wave velocity reflecting the frequency characteristics of the measurement signal of the actual measurement can be accurately calculated. The average pulse wave velocity also has a relatively high correlation value with the result measured using the conventional pulse wave velocity method, and thus the state of the blood vessel can be determined using the evaluation reference in the pulse wave velocity method accumulated from the related art.

Other Embodiments

A program for realizing the evaluation method in the blood vessel state evaluation device according to the present embodiment is also provided. Such a program is recorded on a computer readable recording medium such as a flexible disc to be attached to a computer, a CD-ROM (Compact Disk-Read Only Memory), a ROM, a RAM, and a memory card, and then provided as a program product. Alternatively, the program can be provided by being recorded in a recording medium such as a hard disk built in the computer. The program can also be provided by being downloaded through the network.

The program according to the present invention may call out the necessary modules in a predetermined array at a predetermined timing of the program modules provided as part of the operation system (OS) of the computer and execute the process. In this case, the module is not included in the program itself, and the process is executed in cooperation with the OS. The program not including such a module is also included in the program according to the present invention.

The program according to the present invention may be provided by being incorporated in part of another program such as a program for executing a normal blood pressure measurement. In this case as well, the module included in the other program is not included in the program itself, and the process is executed in cooperation with the other program. The program incorporated in the other program is also included in the program according to the present invention.

The provided program product is installed in a program storage unit such as hard disk, and then executed. The program product includes the program itself and the recording medium on which the program is recorded.

The embodiments disclosed herein are illustrative in all aspects and should not be construed as being restrictive. The scope of the present invention is defined by the claims rather than by the description made above, and all modifications equivalent in meaning to the scope of the claims and within the scope are encompassed therein.

(Appendix Table)

The main shape values of the Avolio model are shown in the following appendix tables.

TABLE 2

| Zone | Zone name | Length (mm) | Radius (mm) | Wall thickness (mm) | Young's modulus (MPa) |
|---|---|---|---|---|---|
| 1 | Ascending aorta | 40 | 14.5 | 1.63 | 0.4 |
| 2 | Aortic arch | 20 | 11.2 | 1.32 | 0.4 |
| 3 | Left subclavian artery | 34 | 4.2 | 0.67 | 0.4 |
| 4 | Common carotid | 89 | 3.7 | 0.63 | 0.4 |
| 5 | Aortic arch | 39 | 10.7 | 1.27 | 0.4 |
| 6 | Brachiocephalic artery | 34 | 6.2 | 0.86 | 0.4 |
| 7 | Internal mammary | 150 | 1 | 0.3 | 0.8 |
| 8 | Subclavian artery | 68 | 4 | 0.66 | 0.4 |
| 9 | Vertebral artery | 148 | 1.9 | 0.45 | 0.8 |
| 10 | Common carotid | 89 | 3.7 | 0.63 | 0.4 |
| 11 | Thoracic aorta | 52 | 10 | 1.2 | 0.4 |
| 12 | Common carotid | 89 | 3.7 | 0.63 | 0.4 |
| 13 | Vertebral artery | 148 | 1.9 | 0.45 | 0.8 |
| 14 | Subclavian artery | 68 | 4 | 0.66 | 0.4 |

TABLE 2-continued

| Zone | Zone name | Length (mm) | Radius (mm) | Wall thickness (mm) | Young's modulus (MPa) |
|---|---|---|---|---|---|
| 15 | Internal mammary | 150 | 1 | 0.3 | 0.8 |
| 16 | Costo-cervical artery | 50 | 1 | 0.3 | 0.8 |
| 17 | Axilliary artery | 61 | 3.6 | 0.62 | 0.4 |
| 18 | Suprascapular | 100 | 2 | 0.52 | 0.8 |
| 19 | Thyrocervical | 50 | 1 | 0.3 | 0.8 |
| 20 | Common carotid | 31 | 3.7 | 0.63 | 0.4 |
| 21 | Thoracic aorta | 52 | 9.5 | 1.16 | 0.4 |
| 22 | Common carotid | 89 | 3.7 | 0.63 | 0.4 |

TABLE 3

| Zone | Zone name | Length (mm) | Radius (mm) | Wall thickness (mm) | Young's modulus (MPa) |
|---|---|---|---|---|---|
| 23 | Thyrocervical | 50 | 1 | 0.3 | 0.8 |
| 24 | Suprascapular | 100 | 2 | 0.52 | 0.8 |
| 25 | Axilliary artery | 61 | 3.6 | 0.62 | 0.4 |
| 26 | Costo-cervical artery | 50 | 1 | 0.3 | 0.8 |
| 27 | Thoraco-acromial | 30 | 1.5 | 0.35 | 1.6 |
| 28 | Axilliary artery | 56 | 3.1 | 0.57 | 0.4 |
| 29 | Circumflex scapular | 50 | 1 | 0.3 | 1.6 |
| 30 | Subscapular | 80 | 1.5 | 0.35 | 1.6 |
| 31 | Carotid | 59 | 1.8 | 0.45 | 0.8 |
| 32 | External carotid | 118 | 1.5 | 0.42 | 0.8 |
| 33 | Superior thyroid artery | 40 | 0.7 | 0.2 | 0.8 |
| 34 | Thoracic aorta | 52 | 9.5 | 1.16 | 0.4 |
| 35 | Superior thyroid artery | 40 | 0.7 | 0.2 | 0.8 |
| 36 | External carotid | 118 | 1.5 | 0.42 | 0.8 |
| 37 | Carotid | 59 | 1.8 | 0.45 | 0.8 |
| 38 | Subscapular | 80 | 1.5 | 0.35 | 1.6 |
| 39 | Circumflex scapular | 50 | 1 | 0.3 | 1.6 |
| 40 | Axilliary artery | 56 | 3.1 | 0.57 | 0.4 |
| 41 | Thoraco-acromial | 30 | 1.5 | 0.35 | 1.6 |
| 42 | Brachial artery | 63 | 2.8 | 0.55 | 0.4 |
| 43 | Lingual artery | 30 | 1 | 0.3 | 0.8 |
| 44 | Internal carotid | 59 | 1.3 | 0.39 | 0.8 |

TABLE 4

| Zone | Zone name | Length (mm) | Radius (mm) | Wall thickness (mm) | Young's modulus (MPa) |
|---|---|---|---|---|---|
| 45 | Facial artery | 40 | 1 | 0.3 | 1.6 |
| 46 | Middle cerebral | 30 | 0.5 | 0.2 | 1.6 |
| 47 | Cerebral artery | 59 | 0.8 | 0.26 | 1.6 |
| 48 | Opthalmic artery | 30 | 0.7 | 0.2 | 1.6 |
| 49 | Coeliac artery | 10 | 3.9 | 0.64 | 0.4 |
| 50 | Abdominal aorta | 53 | 9.5 | 1.08 | 0.4 |
| 51 | Opthalmic artery | 30 | 0.7 | 0.2 | 1.6 |
| 52 | Cerebral artery | 59 | 0.8 | 0.26 | 1.6 |
| 53 | Middle cerebral | 30 | 0.6 | 0.2 | 1.6 |
| 54 | Facial artery | 40 | 1 | 0.3 | 1.6 |
| 55 | Internal carotid | 59 | 1.3 | 0.39 | 0.8 |
| 56 | Lingual artery | 30 | 1 | 0.3 | 0.8 |
| 57 | Brachial artery | 63 | 2.8 | 0.55 | 0.4 |
| 58 | Profunda brachi | 150 | 1.5 | 0.35 | 0.8 |
| 59 | Brachial artery | 63 | 2.6 | 0.53 | 0.4 |
| 60 | Internal carotid | 59 | 0.8 | 0.26 | 1.6 |
| 61 | Gastric artery | 71 | 1.8 | 0.45 | 0.4 |
| 62 | Splenic artery | 63 | 2.8 | 0.54 | 0.4 |
| 63 | Hepatic artery | 66 | 2.2 | 0.49 | 0.4 |
| 64 | Renal artery | 32 | 2.6 | 0.53 | 0.4 |
| 65 | Abdominal aorta | 53 | 5.7 | 0.8 | 0.4 |
| 66 | Superior mesenteric | 59 | 4.3 | 0.69 | 0.4 |

TABLE 5

| Zone | Zone name | Length (mm) | Radius (mm) | Wall thickness (mm) | Young's modulus (MPa) |
|---|---|---|---|---|---|
| 67 | Gastric artery | 32 | 2.6 | 0.53 | 0.4 |
| 68 | Internal carotid | 59 | 0.8 | 0.26 | 1.6 |
| 69 | Brachial artery | 63 | 2.6 | 0.53 | 0.4 |
| 70 | Profunda brachi | 150 | 1.5 | 0.35 | 0.8 |
| 71 | Brachial artery | 63 | 2.5 | 0.52 | 0.4 |
| 72 | Superior ulnar collateral | 50 | 0.7 | 0.2 | 1.6 |
| 73 | Superficial temporal | 40 | 0.6 | 0.2 | 1.6 |
| 74 | Maxilliary artery | 50 | 0.7 | 0.2 | 1.6 |
| 75 | Abdominal aorta | 53 | 5.7 | 0.8 | 0.4 |
| 76 | Maxilliary artery | 50 | 0.7 | 0.2 | 1.6 |
| 77 | Superficial temporal | 40 | 0.6 | 0.2 | 1.6 |
| 78 | Superior ulnar collateral | 50 | 0.7 | 0.2 | 1.6 |
| 79 | Brachial artery | 63 | 2.5 | 0.52 | 0.4 |
| 80 | Inferior ulnar collateral | 50 | 0.6 | 0.2 | 1.6 |
| 81 | Brachial artery | 46 | 2.4 | 0.5 | 0.4 |
| 82 | Common iliac | 58 | 5.2 | 0.76 | 0.4 |
| 83 | Inferior mesenteric | 50 | 1.6 | 0.43 | 0.4 |
| 84 | Common iliac | 58 | 5.2 | 0.76 | 0.4 |
| 85 | Brachial artery | 46 | 2.4 | 0.5 | 0.4 |
| 86 | Inferior ulnar collateral | 50 | 0.6 | 0.2 | 1.6 |
| 87 | Ulnar artery | 67 | 2.1 | 0.49 | 0.8 |
| 88 | Radial artery | 117 | 1.6 | 0.43 | 0.8 |

TABLE 6

| Zone | Zone name | Length (mm) | Radius (mm) | Wall thickness (mm) | Young's modulus (MPa) |
|---|---|---|---|---|---|
| 89 | External iliac | 83 | 2.9 | 0.55 | 0.4 |
| 90 | Internal iliac | 50 | 2 | 0.4 | 1.6 |
| 91 | Internal iliac | 50 | 2 | 0.4 | 1.6 |
| 92 | External iliac | 83 | 2.9 | 0.55 | 0.4 |
| 93 | Radial artery | 117 | 1.6 | 0.43 | 0.8 |
| 94 | Ulnar artery | 67 | 2.1 | 0.49 | 0.8 |
| 95 | Ulnar artery | 85 | 1.9 | 0.462 | 0.8 |
| 96 | Interossea artery | 79 | 0.9 | 0.28 | 1.6 |
| 97 | Radial artery | 117 | 1.6 | 0.43 | 0.8 |
| 98 | External iliac | 61 | 2.7 | 0.53 | 0.4 |
| 99 | External iliac | 61 | 2.7 | 0.53 | 0.4 |
| 100 | Radial artery | 117 | 1.6 | 0.43 | 0.8 |
| 101 | Interossea artery | 79 | 0.9 | 0.28 | 1.6 |
| 102 | Ulnar artery | 85 | 1.9 | 0.462 | 0.8 |
| 103 | Ulnar artery | 85 | 1.9 | 0.46 | 0.8 |
| 104 | Femoral artery | 127 | 2.4 | 0.5 | 0.8 |
| 105 | Profundis artery | 126 | 2.3 | 0.49 | 1.6 |
| 106 | Profundis artery | 126 | 2.3 | 0.49 | 1.6 |
| 107 | Femoral artery | 127 | 2.4 | 0.5 | 0.8 |
| 108 | Ulnar artery | 85 | 1.9 | 0.46 | 0.8 |
| 109 | Femoral artery | 127 | 2.4 | 0.5 | 0.8 |
| 110 | Femoral artery | 127 | 2.4 | 0.5 | 0.8 |

TABLE 7

| Zone | Zone name | Length (mm) | Radius (mm) | Wall thickness (mm) | Young's modulus (MPa) |
|---|---|---|---|---|---|
| 111 | Popliteal artery | 94 | 2 | 0.47 | 0.8 |
| 112 | Popliteal artery | 94 | 2 | 0.47 | 0.8 |
| 113 | Popliteal artery | 94 | 2 | 0.5 | 0.4 |
| 114 | Popliteal artery | 94 | 2 | 0.5 | 0.4 |
| 115 | Anterior tibial artery | 25 | 1.3 | 0.39 | 1.6 |
| 116 | Posterior tibial artery | 161 | 1.8 | 0.45 | 1.6 |
| 117 | Posterior tibial artery | 161 | 1.8 | 0.45 | 1.6 |
| 118 | Anterior tibial artery | 25 | 1.3 | 0.39 | 1.6 |
| 119 | Anterior tibial artery | 150 | 1 | 0.2 | 1.6 |
| 120 | Peroneal artery | 159 | 1.3 | 0.39 | 1.6 |
| 121 | Posterior tibial artery | 161 | 1.8 | 0.45 | 1.6 |
| 122 | Posterior tibial artery | 161 | 1.8 | 0.45 | 1.6 |
| 123 | Peroneal artery | 159 | 1.3 | 0.39 | 1.6 |
| 124 | Anterior tibial artery | 150 | 1 | 0.2 | 1.6 |
| 125 | Anterior tibial artery | 150 | 1 | 0.2 | 1.6 |
| 126 | Peroneal artery | 159 | 1.3 | 0.19 | 1.6 |
| 127 | Peroneal artery | 159 | 1.3 | 0.19 | 1.6 |
| 128 | Anterior tibial artery | 150 | 1 | 0.2 | 1.6 |

The invention claimed is:

1. A blood vessel state evaluation device comprising:
a storage unit for storing a circulatory system model in which a blood vessel located in a living body is divided into a plurality of zones and modeled, the circulatory system model including a shape value representing each of the plurality of zones;
a first measurement unit, adapted for attachment to a first measurement site of the living body, for measuring a time waveform of a first biological signal;
a second measurement unit, adapted for attachment to a second measurement site of the living body, for measuring a time waveform of a second biological signal in synchronization with the first measurement unit;
a first calculating unit for calculating phase difference characteristics of actual measurement based on a phase difference on each frequency component between the first biological signal and the second biological signal, wherein the first calculating unit is configured to calculate the phase difference characteristics of actual measurement using a frequency component in which a coherence value, which is an index indicating a correlation at a frequency region, between the first biological signal and the second biological signal is higher than a threshold value defined in advance;
a second calculating unit for calculating phase difference characteristics between a first transfer function defined based on the circulatory system model in correspondence to a blood vessel passage to the first measurement site and a second transfer function defined based on the circulatory system model in correspondence to a blood vessel passage to the second measurement site, the first transfer function and the second transfer function including an elasticity variable indicating a degree of elasticity of the blood vessel; and
a search unit for determining an optimum elasticity variable by sequentially changing the elasticity variable from an initial value until the phase difference characteristics calculated by the second calculating unit substantially match the phase difference characteristics of actual measurement calculated by the first calculating unit,
wherein the elasticity variable indicates a degree of arterial sclerosis of the blood vessel located in the living body.

2. The blood vessel state evaluation device according to claim 1, further comprising a transfer function calculating unit for calculating the first and second transfer functions based on the shape value of each zone corresponding to the blood vessel passages to the first and second measurement sites, respectively.

3. The blood vessel state evaluation device according to claim 2, wherein the transfer function calculating unit is configured to calculate the first and second transfer functions using a distribution constant model, having a blood pressure of the blood vessel and a blood flow rate as input variables, corresponding to each zone, and wherein each distribution constant model includes a vertical impedance corresponding to easiness in flowing of blood in the corresponding zone, and a horizontal impedance including the elasticity variable.

4. The blood vessel state evaluation device according to claim 1, further comprising a pulse wave velocity calculating unit that is configured to calculate a pulse wave velocity in the blood vessel based on the optimum elasticity variable fitted by the search unit.

5. The blood vessel state evaluation device according to claim 4, wherein the pulse wave velocity calculating unit calculates the pulse wave velocity based on the shape value of each zone corresponding to the blood vessel passage to the first measurement site and the shape value of each zone corresponding to the blood vessel passage to the second measurement site.

6. The blood vessel state evaluation device according to claim 1, wherein the circulatory system model includes a blood vessel diameter and a blood vessel length for the shape value.

7. The blood vessel state evaluation device according to claim 1, wherein the circulatory system model is obtained by dividing the blood vessel located in the living body into a plurality of zones, and then modeling the blood vessel belonging to at least one zone of the plurality of zones.

8. The blood vessel state evaluation device according to claim 7, wherein the blood vessel located in the living body is divided into the plurality of zones based on a size of a blood vessel diameter.

9. The blood vessel state evaluation device according to claim 2, wherein the transfer function calculating unit adds a peripheral part model, in which a blood vessel not modeled in the circulatory system model of the blood vessels contained in each zone is modeled, to the circulatory system model corresponding to each zone, and then calculates the transfer function.

10. The blood vessel state evaluation device according to claim 9, wherein the transfer function calculating unit converts the circulatory system model of each zone based on a shape difference of the blood vessel to calculate the peripheral part model of the zone.

11. The blood vessel state evaluation device according to claim 9, wherein the transfer function calculating unit is configured to calculate the transfer function with a terminating end of the peripheral part model under a non-reflection condition.

12. The blood vessel state evaluation device according to claim 1, further comprising:
a first frequency conversion unit that is configured to calculate first phase characteristics indicating the phase on each frequency component from the first biological signal; and
a second frequency conversion unit that is configured to calculate second phase characteristics indicating the phase on each frequency component from the second biological signal,
wherein the first calculating unit is configured to:
calculate differential phase data by taking a difference of first phase data and second phase data; and
calculate the phase difference characteristics of actual measurement by correcting a phase shift caused by a period delay in the differential phase data in units of phase corresponding to one or more periods.

13. A blood vessel state evaluation method for evaluating a state of a blood vessel located in a living body, the blood vessel state evaluation method comprising the steps of:
storing a circulatory system model, in which the blood vessel located in the living body is divided into a plurality of zones and modeled, in a storage unit,
wherein the circulatory system model includes a shape value representing each of the plurality of zones;
measuring a time waveform of a first biological signal from a first measurement site of the living body and measuring a time waveform of a second biological signal from a second measurement site of the living body;
calculating phase difference characteristics of actual measurement based on a phase difference on each frequency component between the first biological signal and the second biological signal,
wherein in the step of calculating the phase difference characteristics of actual measurement, the phase difference characteristics of actual measurement are calculated using a frequency component in which a coherence value, which is an index indicating a correlation at a frequency region, between the first biological signal and the second biological signal is higher than a threshold value defined in advance;
calculating phase difference characteristics between a first transfer function defined based on the circulatory system model in correspondence to a blood vessel passage to the first measurement site and a second transfer function defined based on the circulatory system model in correspondence to a blood vessel passage to the second measurement site, the first transfer function and the second transfer function including an elasticity variable indicating a degree of elasticity of the blood vessel; and
determining an optimum elasticity variable by sequentially changing the elasticity variable from an initial value until the phase difference characteristics between the first transfer function and the second transfer function substantially match the phase difference characteristics of actual measurement,
wherein the elasticity variable indicates a degree of arterial sclerosis of the blood vessel located in the living body.

14. A blood vessel state evaluation program stored on a non-transitory computer readable recording medium for evaluating a state of a blood vessel located in a living body using a circulatory system model in which a blood vessel located in the living body is divided into a plurality of zones and modeled, wherein
the circulatory system model includes a shape value representing each of the plurality of zones;
a calculation processing unit performing, in response to a command from the program, the steps of:
acquiring a time waveform of a first biological signal at a first measurement site of the living body and acquiring a time waveform of a second biological signal at a second measurement site of the living body;
calculating phase difference characteristics of actual measurement based on a phase difference on each frequency component between the first biological signal and the second biological signal,
wherein in the step of calculating the phase difference characteristics of actual measurement, the phase difference characteristics of actual measurement are calculated using a frequency component in which a coherence value, which is an index indicating a correlation at a frequency region, between the first biological signal and the second biological signal is higher than a threshold value defined in advance;

calculating phase difference characteristics between a first transfer function defined based on the circulatory system model in correspondence to a blood vessel passage to the first measurement site and a second transfer function defined based on the circulatory system model in correspondence to a blood vessel passage to the second measurement site, the first transfer function and the second transfer function including an elasticity variable indicating a degree of elasticity of the blood vessel; and determining an optimum elasticity variable by sequentially changing the elasticity variable from an initial value until the phase difference characteristics between the first transfer function and the second transfer function substantially match the phase difference characteristics of actual measurement, wherein the elasticity variable indicates a degree of arterial sclerosis of the blood vessel located in the living body.

* * * * *